(12) United States Patent
Spaide

(10) Patent No.: US 9,713,424 B2
(45) Date of Patent: Jul. 25, 2017

(54) VOLUME ANALYSIS AND DISPLAY OF INFORMATION IN OPTICAL COHERENCE TOMOGRAPHY ANGIOGRAPHY

(71) Applicant: Richard F. Spaide, New York, NY (US)

(72) Inventor: Richard F. Spaide, New York, NY (US)

( * ) Notice: Subject to any disclaimer, the term of this patent is extended or adjusted under 35 U.S.C. 154(b) by 0 days.

(21) Appl. No.: 15/016,674

(22) Filed: Feb. 5, 2016

(65) Prior Publication Data

US 2016/0228000 A1 Aug. 11, 2016

Related U.S. Application Data

(60) Provisional application No. 62/112,924, filed on Feb. 6, 2015, provisional application No. 62/116,313, filed on Feb. 13, 2015.

(51) Int. Cl.
*A61B 3/14* (2006.01)
*A61B 3/00* (2006.01)
*A61B 3/12* (2006.01)
*A61B 3/10* (2006.01)
*G06T 7/00* (2017.01)
*G06T 15/08* (2011.01)

(52) U.S. Cl.
CPC .......... *A61B 3/1233* (2013.01); *A61B 3/0025* (2013.01); *A61B 3/0041* (2013.01); *A61B 3/102* (2013.01); *G06T 7/0012* (2013.01); *G06T 15/08* (2013.01); *G06T 2200/24* (2013.01); *G06T 2207/10101* (2013.01); *G06T 2207/30041* (2013.01); *G06T 2207/30104* (2013.01); *G06T 2210/41* (2013.01)

(58) Field of Classification Search
USPC ................................. 351/200–246
See application file for complete search history.

(56) References Cited

U.S. PATENT DOCUMENTS

2011/0200242 A1* 8/2011 Takama ................ G06T 7/0016
382/131
2013/0301008 A1* 11/2013 Srivastava ......... G01B 9/02083
351/246

OTHER PUBLICATIONS

Huang D, Swanson EA, Lin CP, Schuman JS, Stinson WG, Chang W, Hee MR, Flotte T, Gregory K, Puliafito CA, et al. "Optical coherence tomography." Science. 1991. pp. 254(5035):1178-81.

(Continued)

*Primary Examiner* — Mohammed Hasan

(57) ABSTRACT

Computer aided visualization and diagnosis by volume analysis of optical coherence tomography (OCT) angiographic data. In one embodiment, such analysis comprises acquiring an OCT dataset using a processor in conjunction with an imaging system; evaluating the dataset, with the processor, for flow information using amplitude or phase information; generating a matrix of voxel values, with the processor, representing flow occurring in vessels in the volume of tissue; performing volume rendering of these values, the volume rendering comprising deriving three dimensional position and vector information of the vessels with the processor; displaying the volume rendering information on a computer monitor; and assessing the vascularity, vascular density, and vascular flow parameters as derived from the volume rendered images.

35 Claims, 21 Drawing Sheets

(56) References Cited

OTHER PUBLICATIONS

Hee MR, Izatt JA, Swanson EA, Huang D, Schuman JS, Lin CP, Puliafito CA, Fujimoto JG. "Optical coherence tomography of the human retina." Arch. Ophthalmol. Mar. 1995. pp. 113(3):325-32.
Fercher AF. "Optical coherence tomography." J. Biomed Opt. 1996. pp. 1(2):157-73.
Drexler W, Morgner U, Kärtner FX, Pitris C, Boppart SA, Li XD, Ippen EP, Fujimoto JG. "In vivo ultrahigh-resolution optical coherence tomography." Opt. Lett. 1999. pp. 24(17):1221-3.
De Boer JF, Cense B, Park BH, Pierce MC, Tearney GJ, Bouma BE. "Improved signal-to-noise ratio in spectral-domain compared with time-domain optical coherence tomography." Opt. Lett. 2003. pp. 28(21):2067-9.
Choma M, Sarunic M, Yang C, Izatt J. "Sensitivity advantage of swept source and Fourier domain optical coherence tomography." Opt. Express. 2003. pp. 11(18):2183-9.
Leitgeb R, Drexler W, Unterhuber A, Hermann B, Bajraszewski T, Le T, Stingl A, Fercher A. "Ultrahigh resolution Fourier domain optical coherence tomography" Opt. Express. 2004. pp. 12(10):2156-65.
Drexler W, Fujimoto JG (eds.) "Optical Coherence Tomography: Technology and Applications." Berlin, Springer. 2008. pp. 1-1346.
Fingler J, Readhead C, Schwartz DM, Fraser SE. "Phase-contrast OCT imaging of transverse flows in the mouse retina and choroid." Invest. Ophthalmol Vis. Sci. 2008. pp. 49(11):5055-9.
Mariampillai A, Standish BA, Moriyama EH, Khurana M, Munce NR, Leung MK, Jiang J, Cable A, Nilson BC, Vitkin IA, Yang VX. "Speckle variance detection of microvasculature using swept-source optical coherence tomography." Opt. Lett. 2008. pp. 33(13)1530-2.
Mariampillai A, Leung MK, Jarvi M, Standish BA, Lee K, Wilson BC, Vitkin A, Yang VX. "Optimized speckle variance OCT imaging of microvasculature." Opt. Lett. 2010. pp. 35(8):1257-9.
Kim DY, Fingler J, Werner JS, Schwartz DM, Fraser SE, Zawadzki RJ. "In vivo volumetric imaging of human retinal circulation with phase-variance optical coherence tomography." Biomed. Opt. Express. 2011. pp. 2 (6):1504-13.
An L, Shen TT, Wang RK. "Using ultrahigh sensitive optical microangiography to achieve comprehensive depth resolved microvasculature mapping for human retina." J. Biomed. Opt. 2011. pp. 16(10):106013.
Conroy L, Dacosta RS, Vitkin IA. "Quantifying tissue microvasculature with speckle variance optical coherence tomography." Opt. Lett. 2012. pp. 37(15):3180-2.
Jia Y, Tan O, Tokayer J, Potsaid B, Wang Y, Liu JJ, Kraus MF, Subhash H, Fujimoto JG, Hornegger J, Huang D. "Split-spectrum amplitude-decorrelation angiography with optical coherence tomography." Opt. Express. 2012. pp. 20(4):4710-25.
Mahmud MS, Cadotte DW, Vuong B, Sun C, Luk TW, Mariampillai A, Yang VX. "Review of speckle and Phase variance optical coherence tomography to visualize microvascular networks." J. Biomed. Opt. 2013. pp. 18 (5):50901.
Jia Y, Bailey ST, Wilson DJ, Tan O, Klein ML, Flaxel CJ, Potsaid B, Liu JJ, Lu CD, Kraus MF, Fujimoto JG, Huang D. "Quantitative optical coherence tomography angiography of choroidal neovascularization in age-related macular degeneration." Ophthalmology. 2014. pp. 121(7):1435-44.
Frangi, A, Niessen, W, Vincken, K, Viergever, M. "Multiscale vessel enhancement filtering. In Wells, W, Colchester, A, Delp, S, (eds.)" 1998. MICCAI. vol. 1496 of Lecture Notes in Computer Science, Springer Berlin /Heidelberg. pp. 130-137.
Krissian, K, Malandain, G, Ayache, N, Vaillant, R, Trousset, Y. "Model based detection of tubular structures in 3d images." Computer Vision and Image Understanding. 2000. pp. 80(2):130-171.
Russ JC. "The Imaging Processing Handbook, Sixth Edition." CRC Press. 2011. pp. 1-885.
Maxime Descoteaux, D. Louis Collins, Kaleem Siddiqi, "A geometric flow for segmenting vasculature in proton-density weighted MRI" Medical Image Analysis 12, p. 497-513 (2008).
Makita S., Hong Y., Yamanari M., Yatagai T., Yasuno Y., "Optical coherence angiography." Opt Express. Aug. 21, 2006;14(17):7821-40.
Zhao Y., Brecke K.M., Ren H., et al., "Three-dimensional reconstruction of in vivo blood vessels in human skin using phase-resolved optical Doppler tomography." IEEE J Sel Top Quantum Electron, 7 (2001), pp. 931-935.
Kehlet Barton J., Izatt J.A., Kulkarni M.D., Yazdanfar S., Welch A.J., "Three-dimensional reconstruction of blood vessels from in vivo color Doppler optical coherence tomography images." Dermatology. 1999;198(4):355-61.

* cited by examiner

 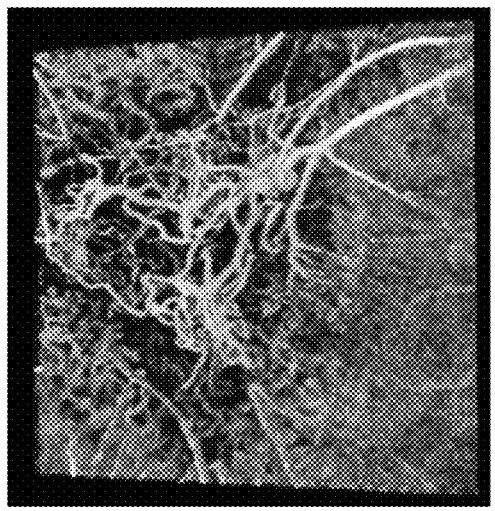
FIG.7A  FIG.7B
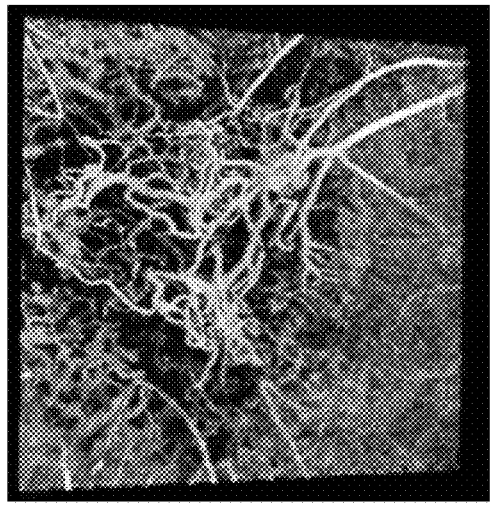 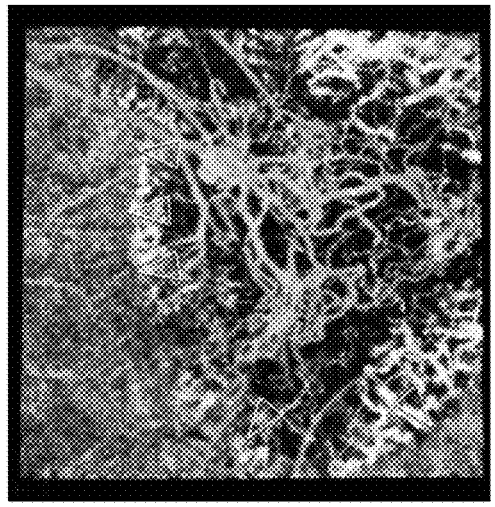
FIG.7C  FIG.7D

VOLUME ANALYSIS AND DISPLAY OF INFORMATION IN OPTICAL COHERENCE TOMOGRAPHY ANGIOGRAPHY

CROSS-REFERENCE TO RELATED APPLICATIONS

This application claims the benefit, pursuant to 35 U.S.C. §119(e), of the respective filing dates of U.S. Provisional Patent App. Ser. No. 62/112,924, filed by me on Feb. 6, 2015, and U.S. Provisional Patent App. Ser. No. 62/116,313, filed by me on Feb. 13, 2015. The entire disclosure of each of said provisional patent applications, and the drawings submitted therewith (both in black and white and in color) are incorporated herein by reference.

BACKGROUND OF THE DISCLOSURE

1. Field of the Disclosure

This application relates generally to optical coherence tomography (OCT) imaging methods and image processing and, more specifically, to an OCT imaging method and processing utilizing volume rendering, and analysis and display of information of the retinal vasculature that utilizes the spatial position of the vessels.

2. Description of Related Art

Optical Coherence Tomography (OCT) is an optical imaging technique that uses interferometry of short-coherence light and processing techniques to capture cross-sectional information from biologic structures with micrometer resolution. (References 1-8 herein incorporated by reference in their entirety.) OCT imaging has been commonly used for non-invasive imaging of objects of interest, such as retina of the human eye.

In OCT imaging, successive one-dimensional scans looking into the tissue ("A-scans") are aggregated into planar scans ("B-scans") and in turn many sequential B-scans can be assembled into a three-dimensional block called a volume scan.

Flow information can be derived from OCT images by looking at phase information or by examining the change over time of phase or amplitude data. In comparing the reflectance images of more than one scan the amount of decorrelation among the images can be calculated on a voxel by voxel basis. Stationary tissue produces reflections having little decorrelation while moving tissue has high decorrelation. Assuming no bulk motion of the patient, motion in the retina is caused by blood flow in retinal vessels. Thus areas of decorrelation of the low-coherence originating signal is indicative of blood flow in vessels running through the examined thickness of the retina. (References 9-17 herein incorporated by reference in their entirety.)

The typical way to display flow information in such a volume of tissue has been to create a virtual 2D image by projecting lines through the volume and selecting the maximal decorrelation value present for inclusion onto the virtual 2D image. This method is called the maximal intensity projection. The resulting 2D image that can be readily evaluated on a computer monitor. By choosing the maximum intensity and collapsing this onto a 2D representation, maximal intensity projection can lose 3D data that is very significant to analyzing the health or disease state of the tissue. An alternate strategy of using the average voxel value suffers the same loss of depth information.

To aid in evaluating the tissue and blood vessels therein the OCT data can be split into anatomic layers through a process called segmentation. The retina is a curved structure, and the flat planes initially produced in OCT slice across many layers, making interpretation difficult. Since retinal layers in a healthy eye have a characteristic and differentiable appearance, it is possible to select boundaries of a layer through a process of segmentation, extending across the lateral topography of the retina. However, since such segmentation is based on structural assumptions relating to healthy tissue. Segmentation algorithms developed for healthy tissue do not work properly for diseased tissue, which may be abnormal in many different ways that are difficult to anticipate in a segmentation algorithm. While segmentation can be useful in a healthy eye, segmentation errors can obscure important disease-related information.

The present disclosure addresses methods that take a different approach to analyzing and visualizing OCT data, seeking instead to visualize vessels through the depth of tissue and to evaluate vascular size, shape, connectivity, and density based on this different type of visualization.

BRIEF SUMMARY OF THE DISCLOSURE

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

In one aspect, the present disclosure describes systems and methods for computer aided visualization and diagnosis by volume analysis of optical coherence tomography (OCT) angiographic data. In one embodiment, such analysis comprises acquiring an OCT dataset using a processor in conjunction with an imaging system; evaluating the dataset, with the processor, for flow information using amplitude or phase information; generating a matrix of voxel values, with the processor, representing flow occurring in vessels in the volume of tissue; performing volume rendering of these values, the volume rendering comprising deriving three dimensional position and vector information of the vessels with the processor; displaying the volume rendering information on a computer monitor; and assessing the vascularity, vascular density, and vascular flow parameters as derived from the volume rendered images. The volume rendering may be performed, for example, by ray casting. Such techniques may be applied to the retina, choroid, optic nerve, and other vascular structures in the eye.

In a further aspect, the foregoing may also incorporate the ability to rotate, shrink, and expand the volume rendered image of the vascular information from various angles and viewpoints. Successions of such views may be recorded as movies.

One may also add performing 3D registration of images obtained over time to obtain vascular flow information related to change over time. This could include, for example, calculating the change in flow over time or pulsatility of flow on either a voxel or feature basis.

Such techniques may be used to generate depictions of the vessels of the eye, wherein morphologic assessment including connectivity of voxels and feature characteristics including fractal dimension are used to classify vessels. These vessels may be segmented and classified by use of a Frangi filter or by methods such as described by Krissian et al. and later authors. (References 18-19 herein incorporated by reference in their entirety.) In such approaches, segmentation of the vascular layers may be accomplished by analysis of the contained vessels.

Qualitative and quantitative estimates of blood flow may be obtained by integration of flow information through the cross-section of the flow data visualized. The vessel flow information and the vascular density as determined by the foregoing methods may be used to derive tissue perfusion information. These can be used to calculate perfusion for a given volume or subvolume of tissue as determined by the vascular density and 2D or 3D segmentation of tissue. In the visual display of such information, the color of the vessels may be coded to show perfusion or flow information. The resulting images and/or data may be used to classify perfusion in the retinal nerve fiber layer as a means to diagnose or monitor glaucoma. Such images and/or data may also be used to classify and grade the perfusion in the retina as a means to diagnose or monitor diabetic retinopathy, artery occlusions, vein occlusions, or other retinal vascular disease. A numerical perfusion index may be derived, that can be used to monitor health and disease of the retina. Deviations from normal values can be displayed numerically or graphically. This is a method superior to using maximal projection or average intensity projection methods and then calculating vessel density of the resultant 2D projection of the vessels.

The flow information resulting from the analysis described above may be shown embedded in volume rendered structural OCT data showing the retinal anatomy. The transparency of the retinal structural OCT image may be modified according to local vascular density and perfusion data. The color of the retinal structural OCT image may be modified according to local vascular density and perfusion data. The tissue, the flow information or any combination may be displayed in a manner to visualize depth information through the tissue sampled. This can include the use of 3D monitors or anaglyph representations. Areas of pathology can also be color coded.

Structural information from the OCT dataset can be segmented and displayed with the flow data in the volume rendering, to place the structural data in the proper anatomic orientation and position in relation to the vessels. The segmented anatomic structures can be color coded or highlighted to increase visualization or recognition to allow visualization, and the volume can be calculated as well.

In one embodiment, a tumor may be segmented in the structural OCT dataset and the vessels in that tumor could be displayed with a different or distinctive color scheme.

These same techniques may be sued to image and evaluate other layers in the eye in addition to the retina to include the choroid and uvea.

The manner of implementation of the foregoing and other aspects of the disclosure should be apparent from the accompanying illustrations and the detailed description that follows.

BRIEF SUMMARY OF THE ACCOMPANYING ILLUSTRATIONS

The following drawings are provided, in which:

FIGS. 7A-7D show four views of volume renderings of OCT angiography data: front view (A), tilting to the left (B) or right (C), and rotated to view from behind (D).

Figure 1:
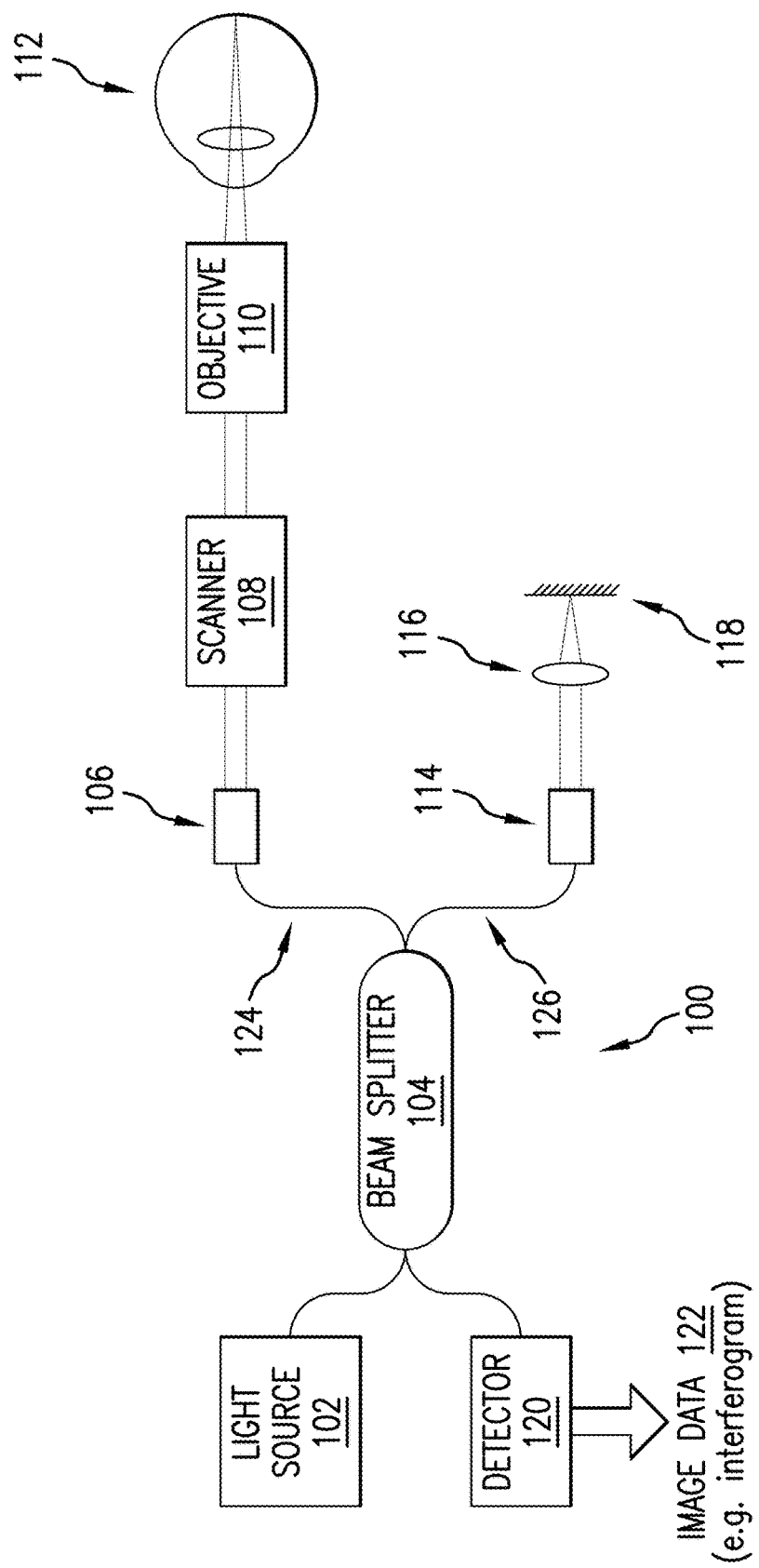
FIG. 1 is a schematic diagram of an OCT imaging system of a type that may be used in connection with certain embodiments described in this disclosure.

FIGS. 2-17E were originally created in color, and have been converted to grayscale for purposes of publication with the present disclosure. Color renditions of these drawings were submitted in connection with the original filings of the above-referenced provisional patent applications. As noted above, the color renditions of the drawings as originally filed with the above-referenced provisional applications have been incorporated herein by reference. It is believed that the accompanying grayscale drawings, together with the textual descriptions of the features and coloration of those drawings as set forth herein, sufficiently disclose the relevant features depicted in the drawings and relied upon to support the present disclosure.

DETAILED DESCRIPTION OF THE DISCLOSED EMBODOMENTS

Certain terminology is used herein for convenience only and is not to be taken as a limitation on the present disclosure. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

A cross sectional OCT image of the retina allows clinicians to evaluate pathology of the eye in vivo. As successively newer OCT instruments have been developed the scan speed has increased. A common unit of measurement of speed of scanning is the A-scan rate, in which an A-scan is a one dimensional representation of reflectance information obtained by a line intersecting tissue. In the case of OCT, the backscatter intensity is measured at discrete points along a line, which in summation produces the A-scan. The A-scan rate of early devices was measured in the hundreds per second and modern commercial instruments can produce up to 100,000 A-scans per second. Many A-scans in a plane produce a B-scan. Successive planes of scans form a three dimensional block of information. The large size of the data set obtained increases the challenge to evaluate the data. It is also possible to slice across the three dimensions of data in any arbitrary direction to extract planes of information that can be evaluated.

The retina is arranged in layers through depth, but its depth is much less than its lateral dimension. The retinal photoreceptors are at the outer aspect of the retina. Successive layers progressing toward the inner portion of the retina contain signal processing cells, and layers that encode information and a layer that sends the information out of the eye to the brain. Visualization of planes of the depth of the retina perpendicular to its surface is called en-face imaging. The problem with simple flat planar cuts through the retina data is the retina is a curved structure lining the inner surface of a sphere. Flat planes slice across many layers making interpretation difficult. Evaluation of B-scans shows each of the retinal layers has a characteristic and differentiable appearance. As such it is possible to select boundaries of a layer through a process of segmentation. Segmentation often is done in B-scans and extended across the lateral topography of the retina by linking the results from successive B-scans. In the process it is possible to use smoothing, noise reduction, and error correction algorithms. Extraction of a tissue plane derived from segmentation isolates specific layers and enables contextual interpretation of abnormalities seen. Specific layers of the retina can be visualized and measured in normal eyes. Evaluating an eye in question can include comparing thickness or volume measurements of layers to nomograms derived from a healthy population. In most applications of en-face imaging, segmentation along retinal layer anatomy has been attempted.

Although an attempt to help in processing and evaluating large datasets, en-face techniques have many limitations. En-face visualization is highly dependent on segmentation. In a healthy eye the layers can be readily differentiated. In disease it is common for blood, fluid, or inflammatory material to expand and distort tissue and alter reflectivity patterns. Segmentation algorithms commonly produce errors in differentiating diseased tissue. Infiltration of tissue into the eye introduces new sources of reflection in addition to distorting extant tissue, thus obviating any segmentation approaches derived from healthy eyes. In any of these situations segmentation and en-face imaging hinders proper visualization of diseased tissue because the data available to view in any one plane is restricted by the errant segmentation result. Pathologic changes occur in three dimensions and typically extend beyond the confines of any given layer.

OCT imaging over stationary tissue produces a relatively constant back reflection. The attributes that can be measured include amplitude and phase information. In addition, comparison of one scan to another from stationary tissue taken a short while later will show a high similarity or correlation in the signals obtained. Moving tissue, which in the case of the retina is blood flow, causes a change in reflection from one moment to the next. The difference between two or more successive scans can be used to generate flow information that is depth resolved. Flow information can be determined from Doppler frequency shifts, phase variance, or changes in the amplitude of the reflections. (References 8-17 herein incorporated by reference in their entirety.) As an example, one method is look at the amplitude correlation in the two signals across the image plane. Scanning over a blood vessel with flow will show a time varying signal, as elements in the blood stream move from one instant to another. The signal obtained over a blood vessel will show a lower amplitude correlation, or conversely a higher amplitude decorrelation, than would stationary tissue. (In addition, the signal would contain phase data, however for simplicity the amplitude decorrelation will be shown by example. The following description would apply to flow information derived from or including phase information.) Comparing multiple points in one B-scan to another obtained over the same area will produce a cross-sectional representation of values corresponding to flow. A look-up table can be constructed to supply display values for any given range of measured values. Using a set of adjacent B-scans allows visualization of flow across a structure; in the case of the retina the retinal vessels will be visualized. In healthy tissue the retinal vessels are constrained to known layers and thus can be visualized by selecting information derived only from those specific layers. In theory it is possible to view the vessels in a volume of tissue, for example the nerve fiber layer, by looking at flow information derived from the volume of tissue occupied by the nerve fiber layer. The typical way to display flow information is to create a virtual 2D image from a volume of tissue by projecting lines through the tissue and selecting the maximal decorrelation value present within the volume onto the virtual 2D image. This method summarizes the flow information in a volume of tissue with a simple 2D image that can be readily evaluated on a computer monitor. This method is called the maximal intensity projection. It is a fast and computationally simple method to show blood flow information and is the currently used method of visualizing retinal OCT angiography data.

Figure 2:
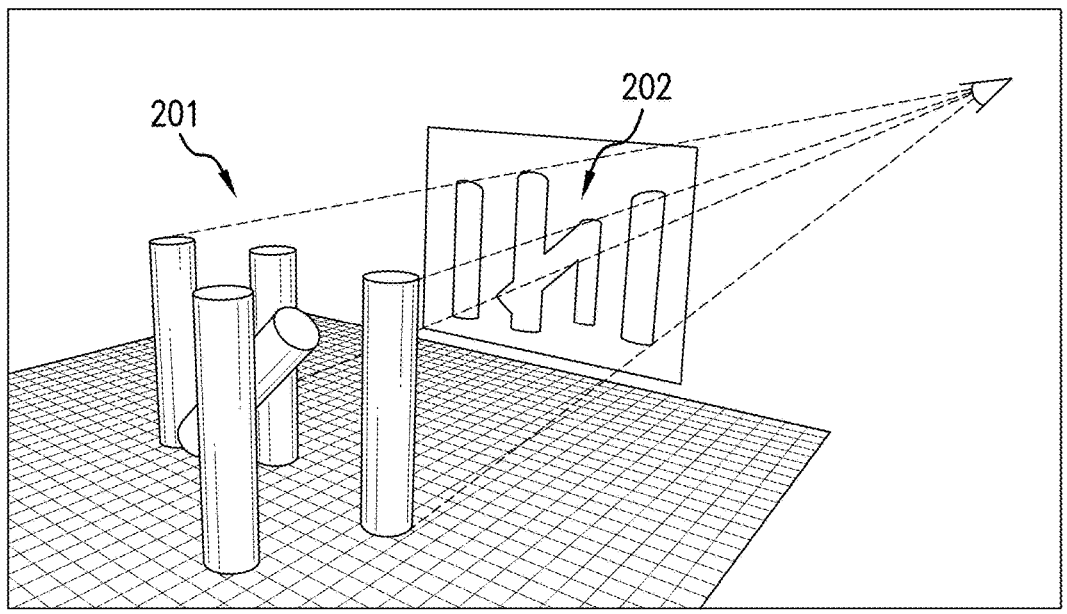
FIG. 2 is a drawing schematically depicting the method of maximal intensity projection.

FIG. 2 is a drawing schematically depicting the method of maximal intensity projection. The structures (201) on the left side of the drawing represent stylized vessels. The flow data generated by OCT angiography occurs through this region and the maximal values are projected to a virtual 2D plane for representation. When the detection algorithm is set to saturate at low flow values there is little dynamic range in the output. This produces a high sensitivity to detect vessels but at the expense of accuracy of rendition. Note the depth information is lost in the maximal intensity projection image and consequently it is not possible to determine if overlapping structures (202) are interconnected or not.

Figure 3:
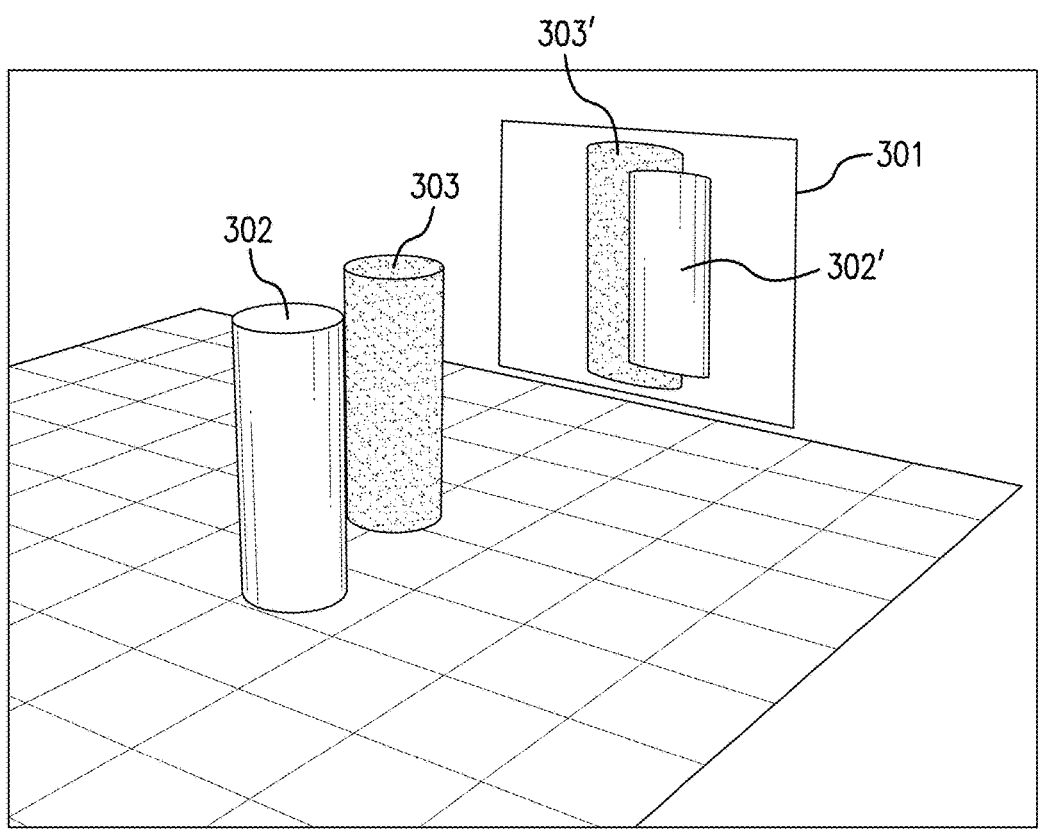
FIG. 3 is a drawing showing an imaging artifact resulting from the technique of maximal intensity projection.

FIG. 3 is a drawing showing an imaging artifact resulting from the technique of maximal intensity projection. Even if the dynamic range is large, the algorithm projects the maximal intensity to form the 2D image (301). Since the bright cylinder (302) has a higher intensity than the gray cylinder (303), it is projected in entirety to the 2D rendering. This creates the impression the order of the bright (302') and gray (303') cylinders have switched places.

Thus, there are several weaknesses of maximal intensity projection that hinder evaluation of tissue. Visualizing the maximal amplitude decorrelation, and thereby flow, along the lines of visualization means the volume visualized is flattened and lesser values of decorrelation are not rendered. (The same argument and those that follow apply to flow measurements obtained from phase information. Reference to amplitude decorrelation is taken to apply to flow signals obtained by any method.) If at a given point of view one vessel is superimposed on another, generally the vessel with the highest flow will be imaged. This can create incorrect renderings of vessel depth. However, since the maximal flow information is projected, it is possible that high flow states within one vessel will provide part of the image while high flow regions of another vessel will provide other parts of the image. This process not only flattens the volume within the region imaged, it also merges flow information between vessels. There are three important consequences of this. First, an underestimation of tissue perfusion will occur since superjacent or subjacent vessels may not be imaged. A second problem with using maximal intensity projection is related to the flattening of the image volume inherent with this technique. Vessels separated in space, but overlapping in the visualized line of sight can appear to be merged. Thus two vessels overlying each other that diverge can appear to be the same as one vessel that branches. In addition, blood vessels that are not related can appear to anastomose. Thus, using maximal projection it is not possible to adequately model blood flow into and out of a volume of tissue. A third main problem with maximal projection techniques are if there are any artifacts that cause decorrelation along a blood vessel, the artifact will appear as part of the vessel. This is problematic, for instance, when pigment is next to a capillary. The pigment often will show a decorrelation signal and being next to the vessel will appear the same as a small aneurysm on the vessel. Any high value of noise in the dataset will be transferred to the rendered image. Any noise in the flow data would be flattened into the average or maximal intensity image and be difficult to remove.

Figure 5:
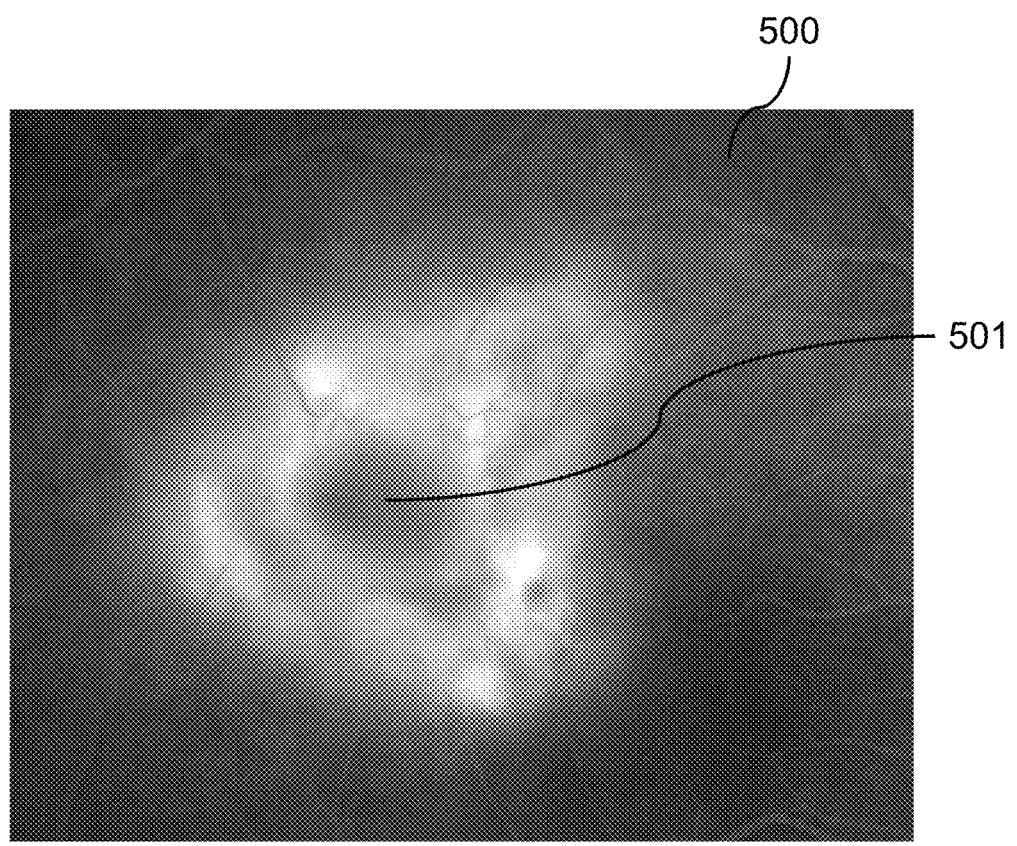
FIG. 5 is a fluorescein angiogram of an eye with neovascular growth secondary to an ocular infection.

FIG. 5 is a fluorescein angiogram (500) of an eye with neovascular growth (501) secondary to an ocular infection. Visualization of the vessels is limited by the optical resolution of the imaging system and the dye leakage from the inflamed vessels.

Figure 6:
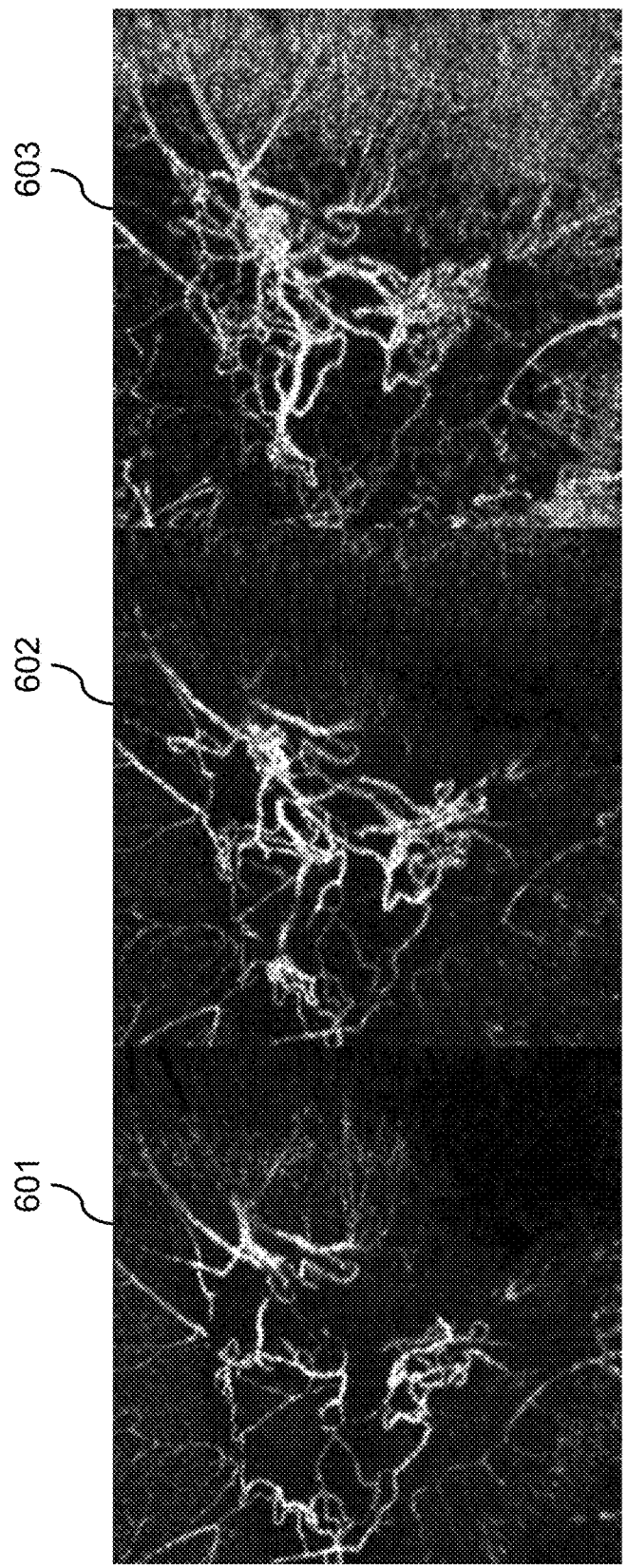
FIG. 6 shows, left-to-right, three en-face OCT angiographic images obtained with maximal intensity projection.

FIG. 6 shows, left-to-right, three en-face OCT angiographic images obtained with maximal intensity projection. These are shown in planes through the lesion illustrated in the fluorescein angiogram. The limited depth information of the en-face evaluation is evident in the successive frames (601, 602, 603) going from left to right.

The three leading causes of blindness in industrialized countries are glaucoma, diabetes, and macular degeneration. The incidence of these conditions is increasing secondary to aging of the population along with increasing dietary and obesity problems. Glaucoma causes damage to the nerve fibers within the eye. These function to conduct visual information from the retina to the brain. The nerve fibers form a compact layer within the inner retina and have high metabolic needs. They are supplied by an arrangement of interconnected capillaries that radiate outward from the optic nerve head and are called the radial peripapillary capillary network. These capillaries are long, straight and occur in closely aligned strata. Because of the vertical overlap segmentation of the nerve fiber layer with maximal intensity projection will not supply correct vessel number, spacing, or flow information. Diabetes damages the blood vessels in the eye and causes aneurysmal changes, vessel loss, and the formation of abnormal vessels that transcend the boundaries established in normal tissue thereby creating difficulty in any conventional segmentation technique. Visualizing the vascular abnormalities of diabetic retinopathy would enable screening programs, estimation of local tissue perfusion, and methods to evaluate treatment. These goals are inhibited by the limitations of current imaging systems. New vessel growth can occur in or under the retina as a consequence of age-related macular degeneration and allied disorders. These vessels grow in multiple layers, do not respect anatomic boundaries of the layers in the eye and therefore are not adequately visualized with en-face segmentation techniques.

Thus, current methods to evaluate the vascularity of the ocular structures are not adequate to provide information concerning health and disease. A proposed goal would be to be able to visualize vessels through the depth of tissue and to evaluate vascular size, shape, connectivity, and density. To accomplish these goals would require a different model than layer segmentation and maximal intensity projection analysis.

In various, non-limiting embodiments disclosed herein, OCT angiographic data obtained throughout a volume of tissue is used as a basis of performing the image processing technique of volume rendering. This allows visualization of the depth of the vessels as well as providing for the opportunity to have lighting and shading parameters specified for optimal visualization.

Figure 4:
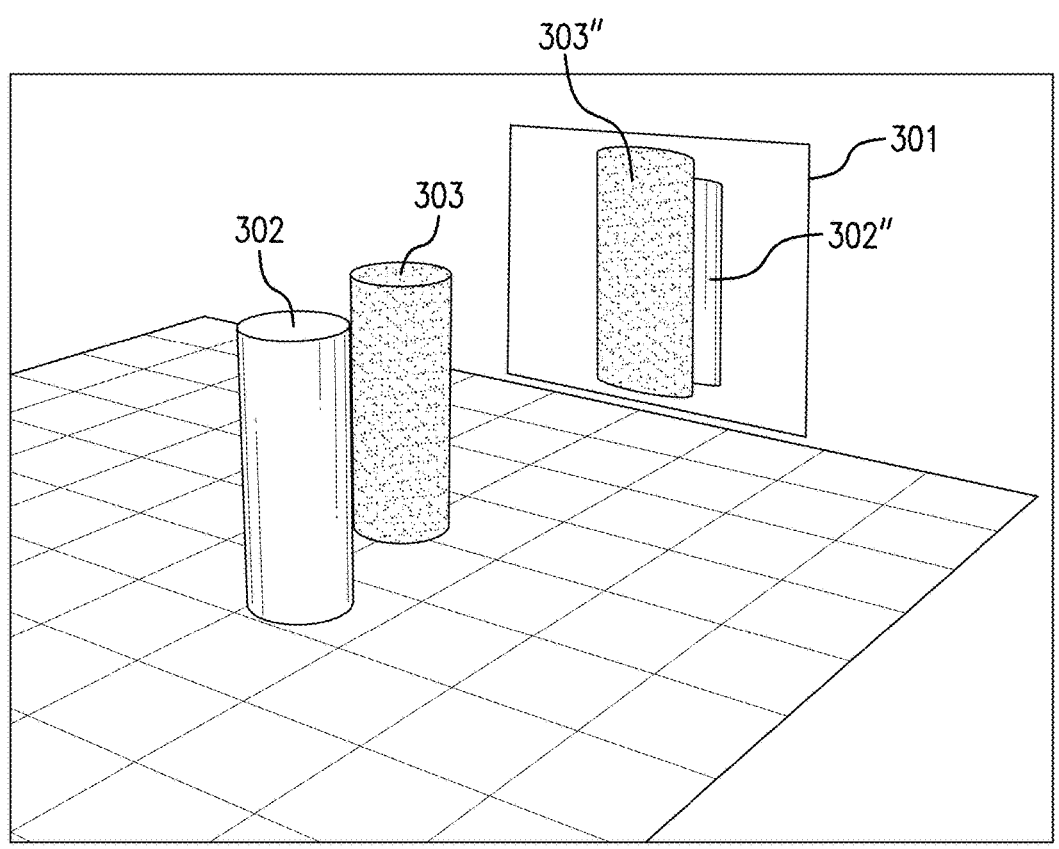
FIG. 4 is a drawing and accompanying brief explanation of a volume rendering of the structures shown in FIG. 3, wherein the correct orientation of the depicted features is preserved.

For example, FIG. 4 shows a drawing of a volume rendering of the structures shown in FIG. 3, displaying the advantage that the correct orientation of the depicted features (302, 303, 302", 303") is preserved.

Using volume rendering, the vascular density, vascular diameter, and flow characteristics of the retinal circulatory system can be quantified and displayed as variations in color, transparency, or as overlays. Viewing the displayed data can be enhanced by rotation or magnification. Blood vessels provisionally can be classified by flow data and by the variance of the flow data over time. These vessels may be further evaluated by examining their tubularity and connectivity to adjacent voxels. Noise may be removed by using 3D methods. The data may also be viewed by providing depth information as by using 3D monitors or anaglyph images. The vessels information can be embedded in volume rendered reflectance images of tissue.

According to one of more aspects described herein, during scan capture with an OCT imaging system the scan data is stored as raw data is used as a basis for volume rendering. Volume rendering techniques such as ray casting are used to create a 3D representation of the data. The visualization, analysis, and display of the data retains the three dimensional information.

FIG. 1 illustrates an exemplary, non-limiting OCT imaging system 100 in which one or more aspects described herein can be implemented. FIG. 1 is a simplified depiction of an OCT imaging system intended to provide a general structural overview and does not necessarily represent a complete implementation of an imaging system. For example, optical elements such as polarization controllers, additional beam splitters, other light paths, etc., are omitted for clarity. For instance, the schematic illustration of FIG. 1 is intended to generally encompass various OCT implementations such as, but not limited to, time-domain OCT, spectral-domain OCT, and/or swept-source OCT since the techniques described and claimed herein can be utilized in connection with substantially any form of OCT imaging.

In general, OCT operates according to the same basic principles as ultrasound but utilizes light as a medium whereas ultrasound utilizes sound. That is, OCT images the subject by irradiating the subject with light and measuring a time delay and intensity of reflected light. However, light is much faster than sound. So, unlike the time delay in an ultrasound echo, the time delay of the reflected light is not directly measured. Instead, OCT utilizes low-coherence interferometry to detect time differences corresponding to distances between structures of the subject. Particularly, a low-coherence broadband light source is split into a sample portion and a reference portion. The reference portion travels a path toward a reference (i.e., a reference mirror) while the sample portion is directed towards the subject (e.g., an eye and, specifically, the retina). When a distance traveled by the sample portion and a corresponding reflection off the subject is within a coherence length of a distance traveled by the reference portion and its corresponding reflection, an interference pattern is generated. The interference pattern indicates an intensity of light at a certain depth of the subject, which in turn, facilitates generating image data pertaining to the subject.

To derive intensity information at varying depths of the subject, several different techniques can be utilized. In one technique, referred to as time-domain OCT, the travel distance of the reference portion is modulated to scan different depths. For example, the reference mirror can be oscillated to change the travel distance. Other techniques, which can be collectively referred to as frequency-domain OCT, do not require alterations to the reference portion. In these techniques, various wavelengths can be encoded, spatially or temporally for example, where different detected frequencies of interference signal correspond to different depths within the subject. A Fourier analysis on a received signal that represents reflected intensities at different frequencies generates the intensities reflected at different depths at a point of the subject.

According to one example of a frequency-domain OCT technique (commonly referred to as Fourier-domain or spectral-domain OCT), a reference interference pattern is dispersed into individual wavelength components by a grating or other such dispersive means. Conceptually, an array of photodetectors, each sensitive to a specific range of wavelengths, simultaneously detects respective intensities of the frequency components corresponding to different depths at a scanned point of the subject. In conventional practice, however, typically a charge couple device (CCD) or complimentary metal-oxide-semiconductor (CMOS) line camera or spectrometer is utilized and the grating physically separates the different wavelengths of light. In another example, referred to as swept-source OCT, a tunable light source is utilized to scan over different wavelengths. The intensities at each scanned wavelength can be collected by computer processor apparatus and transformed by a Fourier analysis to generate an intensity profile that details intensities at various depths. The sensitivity of these modalities is greatly enhanced over older time domain instruments.

In an aspect, the OCT imaging system 100 in FIG. 1 is configured to generate cross-sectional images of portions of an eye 112 including the retina, sclera, choroid, vitreous, cornea, iris, crystalline lens, and/or the entire eye 112. Such images are generated, generally, by impinging light from light source 102 onto the portions of the eye 112 and observing reflected light. Light source 102 can be a low-coherence broadband in the case of spectral-domain OCT or a tunable laser in the case of swept-source OCT. Light emitted from light source 102 is split by an optical adaptor such as a beam splitter 104 into two portions: a sample portion 124 that travels toward the eye 112, and a reference portion 126 that travels along a path toward a reference reflector. As shown in FIG. 1, the reference portion 126 can include a fiber optic cable leading to a collimator 114, which transmits the light from light source 102 to an optical element, such as lens 116, for focusing onto a reference mirror 118. Similarly, the sample portion 124 can follow a fiber optic cable to a collimator 106, which transmits light to a scanner 108. Scanner 108 is configured to direct or scan the light over various points of a surface of the eye 112. In particular, scanner 108 enables a two-dimensional (2D) scan of a focal plane established within the eye 112 by an objective 110. The objective 110, as described in greater detail below, enables a focal plane for the sample portion 124 to be adjusted to substantially any depth of the eye 112.

According to the principles of OCT, when a distance traveled by the sample portion and a corresponding reflection off the subject is within a coherence length of a distance traveled by the reference portion and its corresponding reflection, an interference pattern is generated. The interference pattern is detected by detector 120 and output to the processor as image data 122, e.g., an interferogram. The interference pattern encodes intensity information for portions of the eye 112 which are depth encoded in the interferogram.

Under control of a processor, a scanning mechanism performs a raster scan through the tissue. At each locus on the scan plane an A-scan is obtained. The beam of light enters the tissue and various surfaces, structures, or material reflects a portion of the light back out of the eye. This backscattered light is compared to a reflection from a reference arm and the interferogram is spectrally dispersed by an optical grating, in the case of spectral domain OCT, and a line CCD records the intensity of the spectral components. The recorded signal is analyzed, by a processor, by a Fourier transform. The result is a depth resolved reflectivity profile along the A-scan line. Sequential scanning of multiple A-scans across a plane produces a B-scan. A set of B-scans obtained in succession produces a volume of data that can be analyzed by image processing techniques (reference 18 herein incorporated by reference in its entirety).

In ray casting, also performed by a processor, lines emanate from a viewing position through a 2D plane and then into the tissue dataset. The value of the intersection of the ray through the 2D representation is a function of the densities and lighting through which the line transverses. Rotation of the dataset would produce a corresponding change of the contained elements in the display space. The values of any one voxel can be evaluated in isolation and in comparison to neighboring voxels to derive tissue specific information. Every voxel contributes to the information displayed, not a selection of the voxels representing the highest decorrelation. A less desirable way to obtain 3D information concerning the retinal vasculature would be to use thin sections of the retinal data, obtained using a metric such as the maximal intensity projection or average intensity projection in each vertical aggregate of voxels, and assemble an image from those sections. The retina is typically 250 microns thick in health and at most several times thicker in disease states. The axial point spread function for OCT usually approximates the axial resolution and for clinical instruments is 5 to 7 microns. Using slices one or more times the thickness of the axial point spread function can reduce the number of planes that need to be processed for the volume rendering, thus reducing computational overhead. However, this comes at the price of decreased axial resolution. The resultant dataset, which in a healthy eye may only represent 25 slices, can be visualized using a number of computerized techniques including volume rendering.

A system for computer aided visualization and diagnosis as described above may comprise an imaging system under the control of at least one processor for acquiring an OCT dataset from a volume of anatomical tissue; software stored on a computer-readable medium accessible to the at least one processor, containing instructions to cause the at least one processor to: evaluate the dataset for flow information using amplitude or phase information; generate a matrix of voxel values, representing flow occurring in vessels in the volume of tissue; perform volume rendering of these values by deriving three dimensional position and vector information of the vessels; and display the volume rendering information on a computer monitor.

The analytic functionality described herein may be provided separately via software. For example, a non-transitory computer readable medium containing such software may have recorded therein instructions to cause a processor to acquire from an imaging system an OCT dataset from a volume of anatomical tissue; evaluate the dataset for flow information using amplitude or phase information; generate a matrix of voxel values, representing flow occurring in vessels in the volume of tissue; perform volume rendering of these values by deriving three dimensional position and vector information of the vessels; and display the volume rendering information on a computer monitor. Additional instructions may be provided to perform various other and further functions as described herein.

Whereas maximal intensity projections specifically isolate the largest decorrelation in a given line of sight as a way to show vessels versus no vessel in a region of tissue. However, evaluation of voxel values within a vessel can provide a method to estimate flow in a vessel. This is lost in maximal intensity projection. Computerized integration of voxel flow information over the image of blood vessel can provide qualitative and quantitative estimates of blood flow in that vessel, and these estimates can be represented as a qualitative or quantitative overlay on a 3D image. The vessel flow information and vascular density so determined may be used to derive tissue perfusion information in a volume of selected tissue. The vessels may be color coded, by the processor, to show perfusion or flow information. The integration data may be visually represented on the computer monitor in orthogonal planes to show regional perfusion status. In one embodiment, the qualitative and quantitative estimates of blood flow may be obtained by integrating the blood flow information through cross-sections of the flow data visualized. The vascular density per unit volume of tissue can be calculated. The retinal nerve fiber layer has the potential for loss or damage in diseases such as glaucoma. The thickness and composition of the nerve fiber layer can be impacted as a consequence. Measurement of the nerve fiber layer thickness is a common test in evaluating glaucoma. The pathologic change in glaucoma is the loss of the nerve fibers, but concurrent cellular proliferation within that layer, such as by glial cells may confound thickness measurements. The loss in thickness by death of nerve fibers would be partially offset by glial cell proliferation, which is not uncommon after neural injury. The nerve fibers are highly active metabolically and are supported by a dense network of capillaries. Glial cells are not as metabolically active and do not require as high a blood vessel density. Measuring the associated capillaries along with the thickness can provide layer specific estimates of the vascular density and indirectly the health of the nerve fiber layer. Classifying perfusion in the retinal nerve fiber layer may be used as a means to diagnose or monitor glaucoma. Classifying and grading the perfusion in the retina may also be used to diagnose or monitor diabetic retinopathy, artery occlusions, vein occlusions, or other retinal vascular disease. A numerical perfusion index may be derived from this data and used to monitor health and disease of the retina. The visual display of this information may include numerical or graphic indications showing deviations from normal values.

The flow values of specific voxels, particularly in the context of which they occur, can be used to classify various types of tissue. Areas of no or low flow values represent an absence of flow, generally taken to mean an absence of vessels. High regions of flow signal represent flow, which occurs in a vessel. The values of the voxels at the boundary region of the vessel would be expected to form a transition between the low and high values of flow signal. This edge can be established through common image processing techniques such as, but not limited to using a 3D Laplacian kernel, which is a discrete implementation over the volume of the kernel that produces a spatial second derivative of the image. More sophisticated methods that are less prone to noise include the Sobel operator or the Frangi vesselness estimation. Once the edges of the vessel are defined the flow values within the confines established represent blood flow within the imaged vessel. The values within the 3D representation of the vessel are evaluated. Vessels with low decorrelation values for any given size can be classified as veins, high decorrelation as arteries and the smallest vessels as capillaries. Given the depth resolved classification of blood flow inherent with this technique, it is possible to differentiate true vascular anastomosis from vascular overlay. A desirable feature would be able to evaluate the vessels over time as a means of grading blood flow, disease progression, and response to treatment. A preferred method to obtain this result is 3D deformable image registration. Changes in decorrelation values over small intervals of time are likely due to the pulsatile nature of blood flow. Rapid succession of OCT images can be analyzed and vessels with the combination of high decorrelation values and also with a large variance of decorrelation values are experiencing not only high flow, but high pulsatility. Change in flow over time or pulsatility of flow may be calculated on either a voxel or feature basis. Quantification of the pulsatility of the vessels in the eye can provide information about the impedance of the vessels in the circulatory circuit. Very short term changes would be pulsatility, but changes over time could indicate disease progression. For example, over time diabetics lose blood vessels in the retina. So comparison of two volumes of vessels could show regional differences in perfusion. Changes over longer periods of time may be used to evaluate the circulatory system or to monitor disease progression. The flow information can be used to create look-up tables that would color code the vessels to supply classification information. The color coding could be used to show the certainty of the classification as well. For example, arteries can be coded as red, veins blue, both based on high certainty of classification. A vessel in between in terms of certainty can be color coded using the range of colors between red and blue. In an additive color system magenta is compose of equal parts red and magenta. Redder variants of magenta can be used to color code vessels that are probably arteries and bluer variants those that are probably veins.

The three dimensional connectivity of high value voxels can be used to reduce image noise and improve tissue classification. Noise reduction such as using a 3D rolling ball filter can remove isolated bright voxels that are not connected to other bright voxels. The isolation and visualization of vessels is dependent on volume rendering along with manipulation of transparency transfer function. Some forms of noise are a statistical function and not likely to affect multiple consecutive voxels along a line of sight, and thus will be minimized in a volume rendering. After volume rendering, voxels can be interrogated for local connectivity with adjacent high value voxels as blood flow occurs in a circuit and flow cannot occur in an isolated voxel. Non-connected high value voxels can be suppressed. Subsequent thin slabs or 2D slices through the rendered volume would have lower noise. The connectivity and patterning of vessels can serve as tissue specific characteristics that can be used to segment tissue. Current methods, by contrast, attempt to classify the tissue first then visualize the vessels.

The vessels in the inner retina show a fractal branching pattern with a segment length that is proportional to the segment radius and branching angles that are a function of the relative radii of the daughter branches. There is a deeper plexus of vessels in the retina that appears as a curvilinear mesh of relatively small diameter vessels. Vessels classification and layer segmentation can be performed by features of the contained vessels. Deviations form normality can be evaluated by visual inspection or by mathematical modeling. Retinal diseases commonly cause distortion or loss of layers and thus even if those distortions would prevent proper visualization with enface techniques.

Disease processes involving the eye, particularly the retina can affect multiple layers and consequently cannot be visualized with segmentation techniques. Many of these diseases directly involve new vessel formation or contain highly characteristic new vessels. A desired methodology would be able to provide visualization of the vascular elements in three dimensions. A preferred method is to use volume rendering to obtain three dimensional models of the vascular abnormalities.

Because of the complexity of the resultant dataset, display of the rendered image can take various forms. Since the dataset can be shown from multiple viewpoints it is possible to display two images from differing viewpoints to obtain a true visualization of depth. This can occur with the use of red-cyan anaglyph images or more sophisticated methods using 3D monitors. In addition to showing depth by stereo effect various layers of vessels can be color encoded. In one implementation the vessels in the inner retina were rendered blue, the deep plexus was rendered in red and vessels that infiltrated into deeper layers were yellow. To aid visualization of the deeper layers of vessels it is possible to alter the transparency function of the overlying vessels.

In one embodiment, the transparency of the volume rendered image may be modified according to local vascular density and perfusion data. The tissue, the flow information or any combination may be displayed in a manner to visualize depth information through the tissue sampled. This can include the use of 3D monitors or anaglyph representations. Areas of pathology may be color coded. The transparency can be varied by layer or depth. For example, to be able to see deeper layers we can increase the transparency of the overlying layers.

To put the layers of vessels into an anatomic context it is possible to create volume rendered representations of the tissue and then embed the OCT angiographic image into that. The opacity function of the volume rendered reflectance image can be adjusted to allow visualization of the vessels. The color and opacity of the tissue shown in the volume rendering of the reflectance image can be altered in relation to the vascular density, perfusion estimates, or deviation from normality to allow judgment of health and disease.

Structural information from the OCT dataset can be segmented and displayed with the flow data in the volume rendering. This places the structural data in exact anatomic orientation and position in relation to the vessels since the flow data was derived from the structural OCT dataset. The resultant vascular flow parameters may be shown embedded in the structural OCT data showing the retinal anatomy. The segmented anatomic structures can be color coded or highlighted by other methods to increase recognition and facilitate visualization, and the volume can be calculated as well. The volume of the segmented anatomic structures may be calculated. Reflective or morphologic characteristics such as gray scale values, diameter, circularity, or more sophisticated analysis such as use of Frangi filters may be used in generation of automatic classification of the structural features segmented.

Regions of what could be normal or abnormal vascularity in terms of vessel density may be specifically highlighted in relation to structural OCT findings. In one embodiment, a tumor may be segmented in the structural OCT dataset and the vessels in that tumor could be displayed with a different or distinctive color scheme. Conversely the intervascular tissue can be color coded as well.

Figure 8:
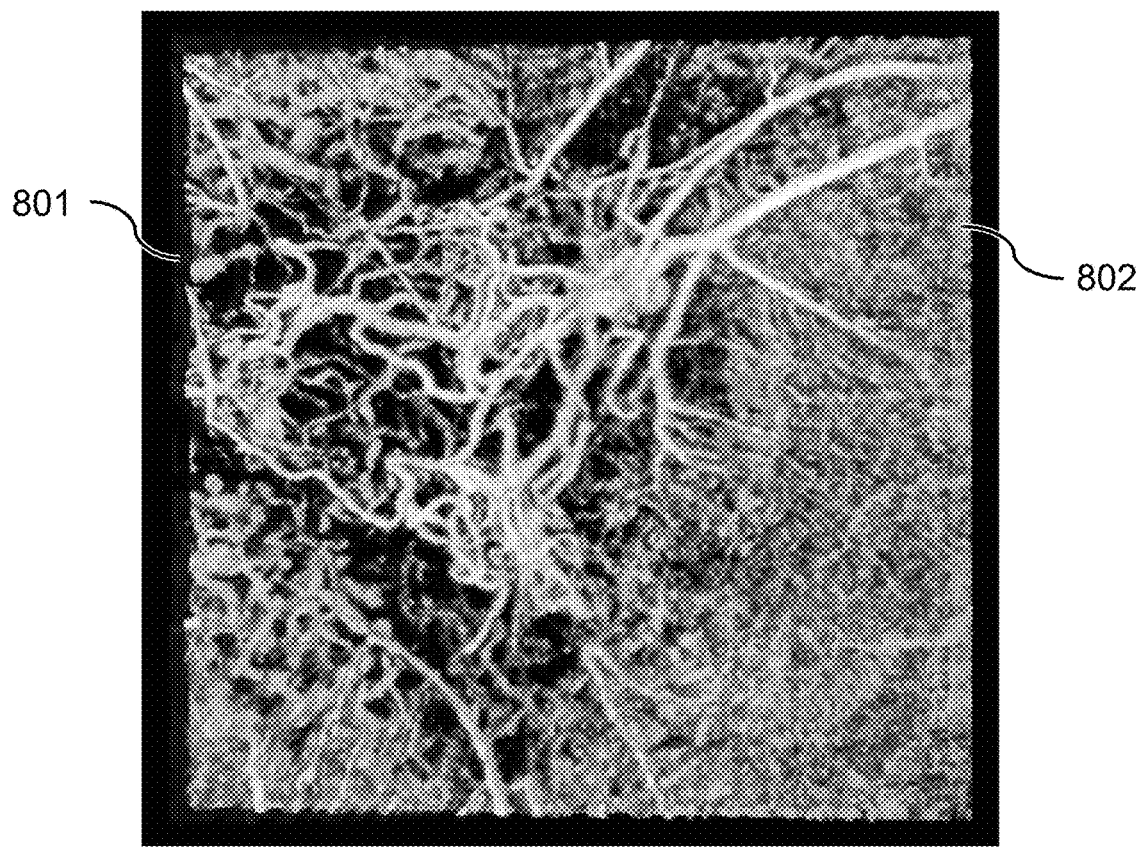
FIG. 8 shows an anaglyph image rendered with red and cyan images to show the depth of the lesion.
Figure 9:
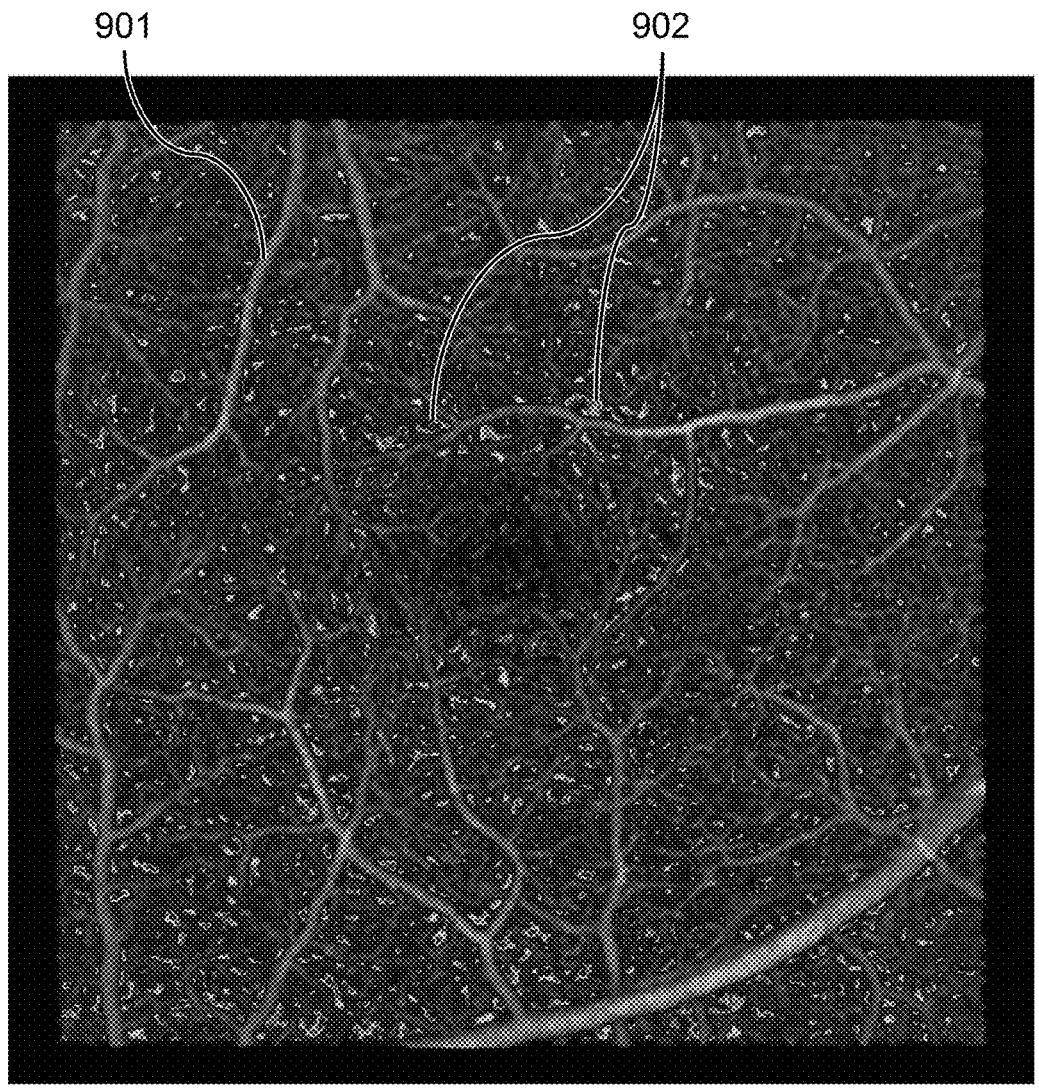
FIG. 9 shows a top view of a volume rendering of the vasculature of a normal eye in which the inner retinal vessels are colored blue and the deep plexus, red.
Figure 10:
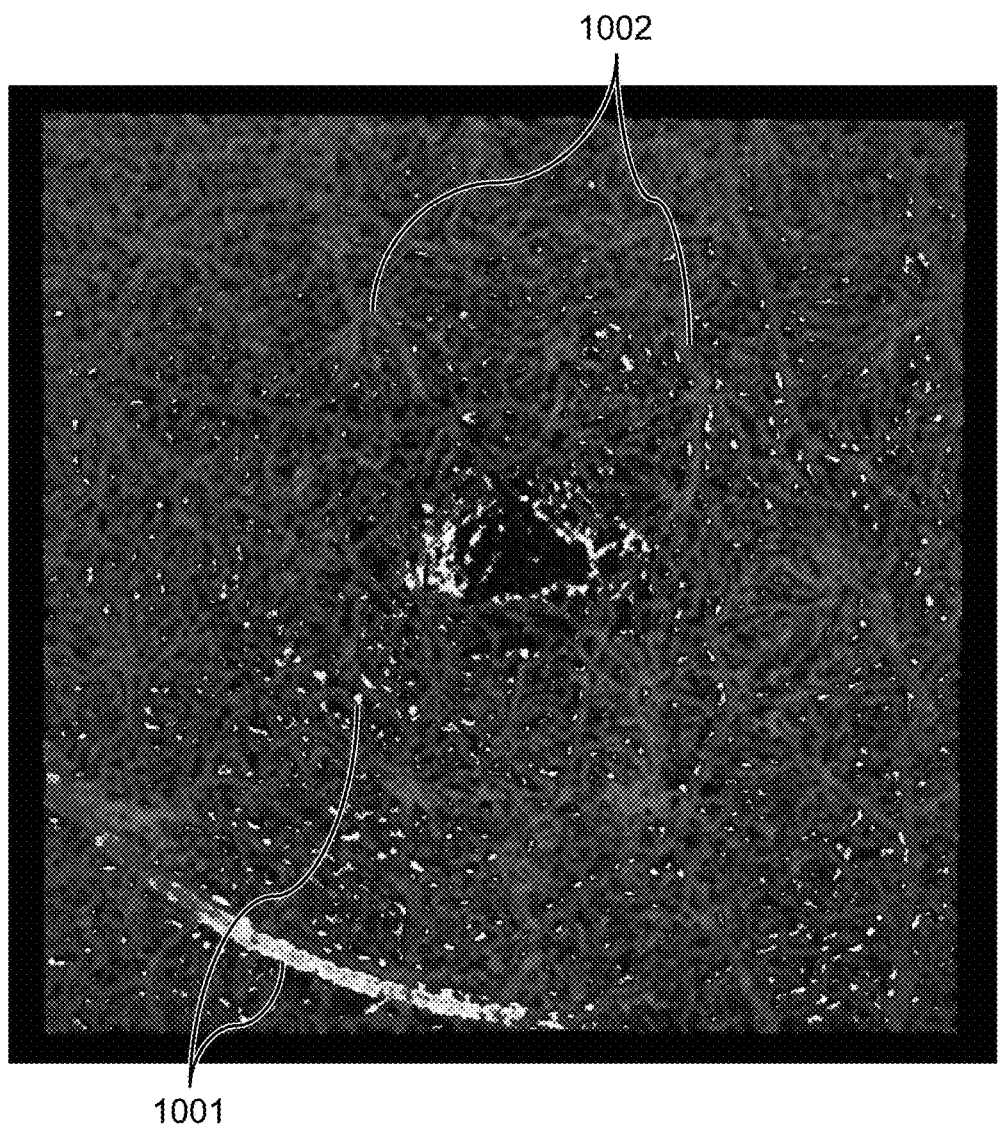
FIG. 10 shows a bottom view of a volume rendering of the vasculature of a normal eye in which the inner retinal vessels are colored blue and the deep plexus, red.
Figure 11:
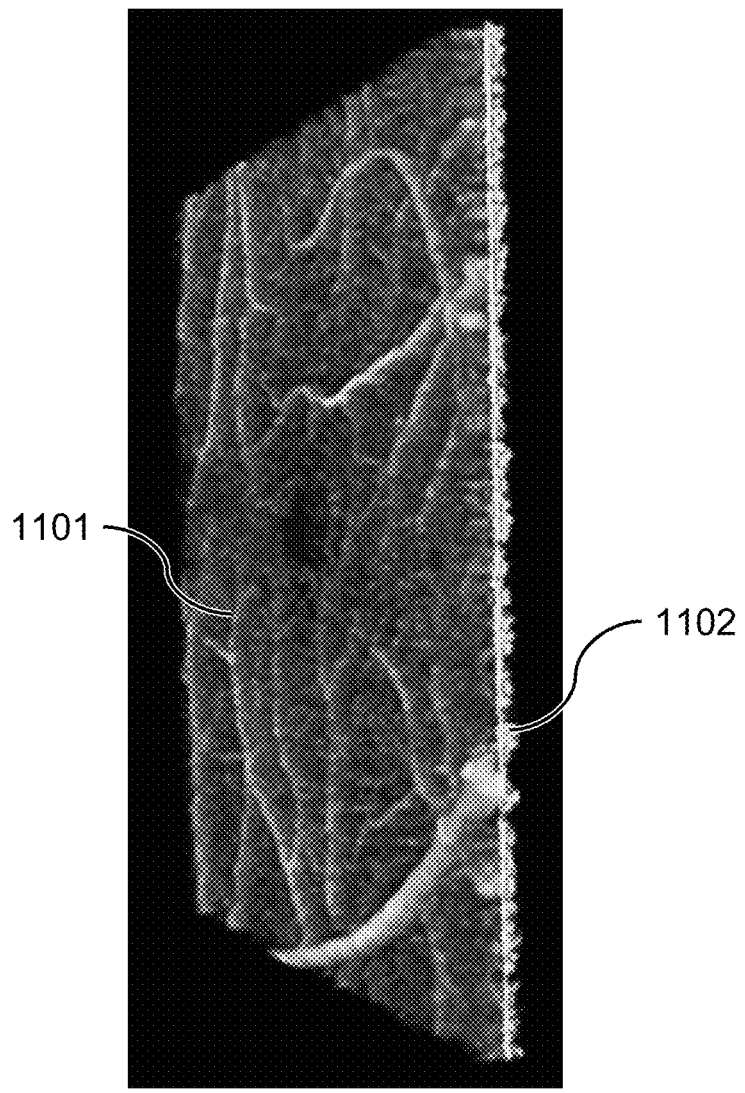
FIG. 11 shows an image rendered from an oblique orientation of the vasculature of a normal eye in which the inner retinal vessels are colored blue and the deep plexus red.

Examples of computer generated volume renderings of OCT data are shown in FIGS. 7A-11. FIGS. 7A-7D show four views of volume renderings of OCT angiography data: front view (A), tilting to the left (B) or right (C), and rotated to view from behind (D). FIG. 8 shows an anaglyph image rendered with red (801) and cyan (802) images to show the depth of the lesion. FIG. 9 shows a top view of a volume rendering of the vasculature of a normal eye in which the inner retinal vessels (901) are colored blue and the deep plexus (902), red (the red appears as lighter areas in the grayscale rendering of FIG. 9). FIG. 10 shows a bottom view of a volume rendering of the vasculature of a normal eye in which the inner retinal vessels (1001) are colored blue and the deep plexus (1002), red (the blue is shown as the lighter areas in the grayscale rendering of FIG. 10). FIG. 11 shows an image rendered from an oblique orientation of the vasculature of a normal eye in which the inner retinal vessels (1101) are colored blue and the deep plexus (1102) red. The rendered image is viewed from an oblique orientation (the red appears as the brighter area along the right edge in the grayscale rendering of FIG. 11).

Figure 12:
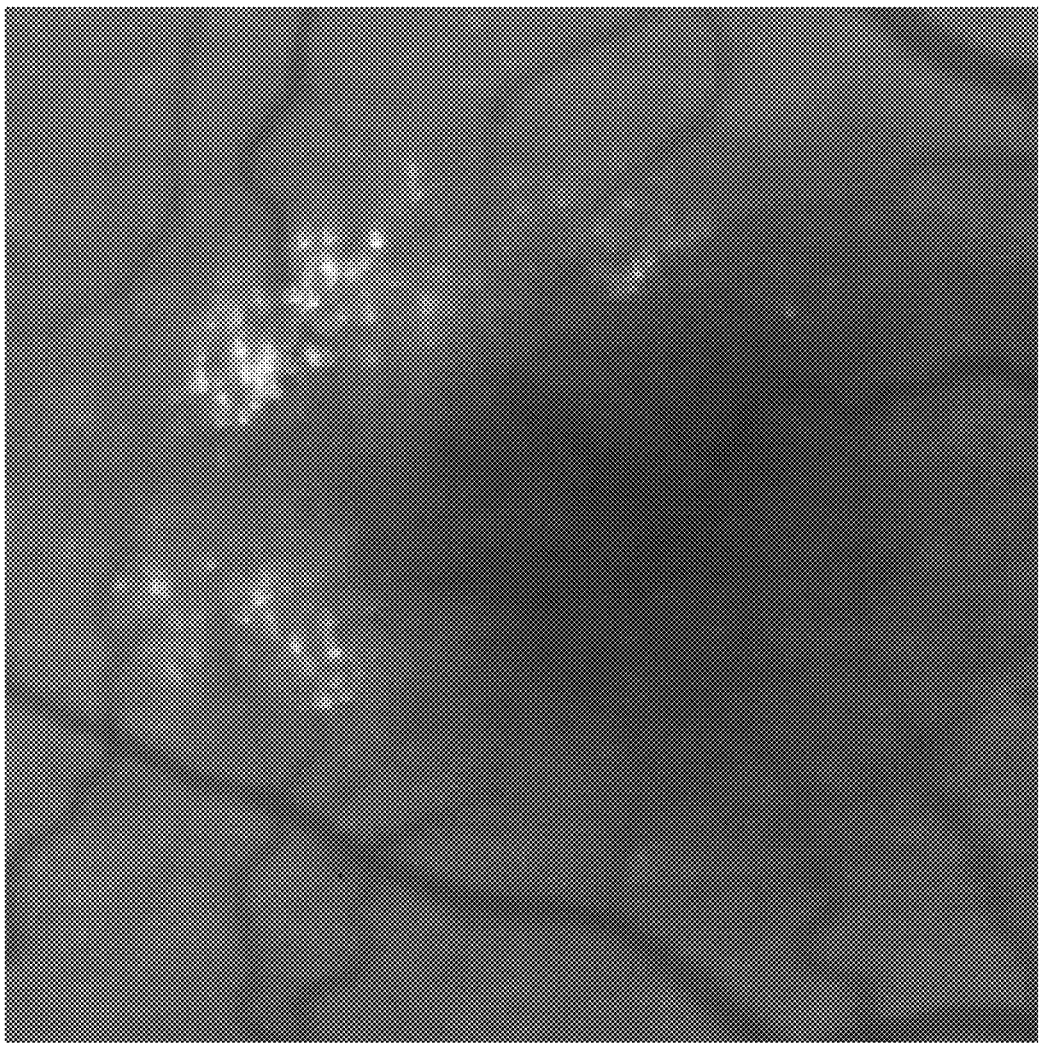
FIG. 12 is a color photograph of an eye with macular telangiectasis.

FIG. 12 is a color photograph of an eye with macular telangiectasis. The quality of the photograph is limited by the optical resolution of the fundus camera and the cataract present in the patient's eye.

Figure 13:
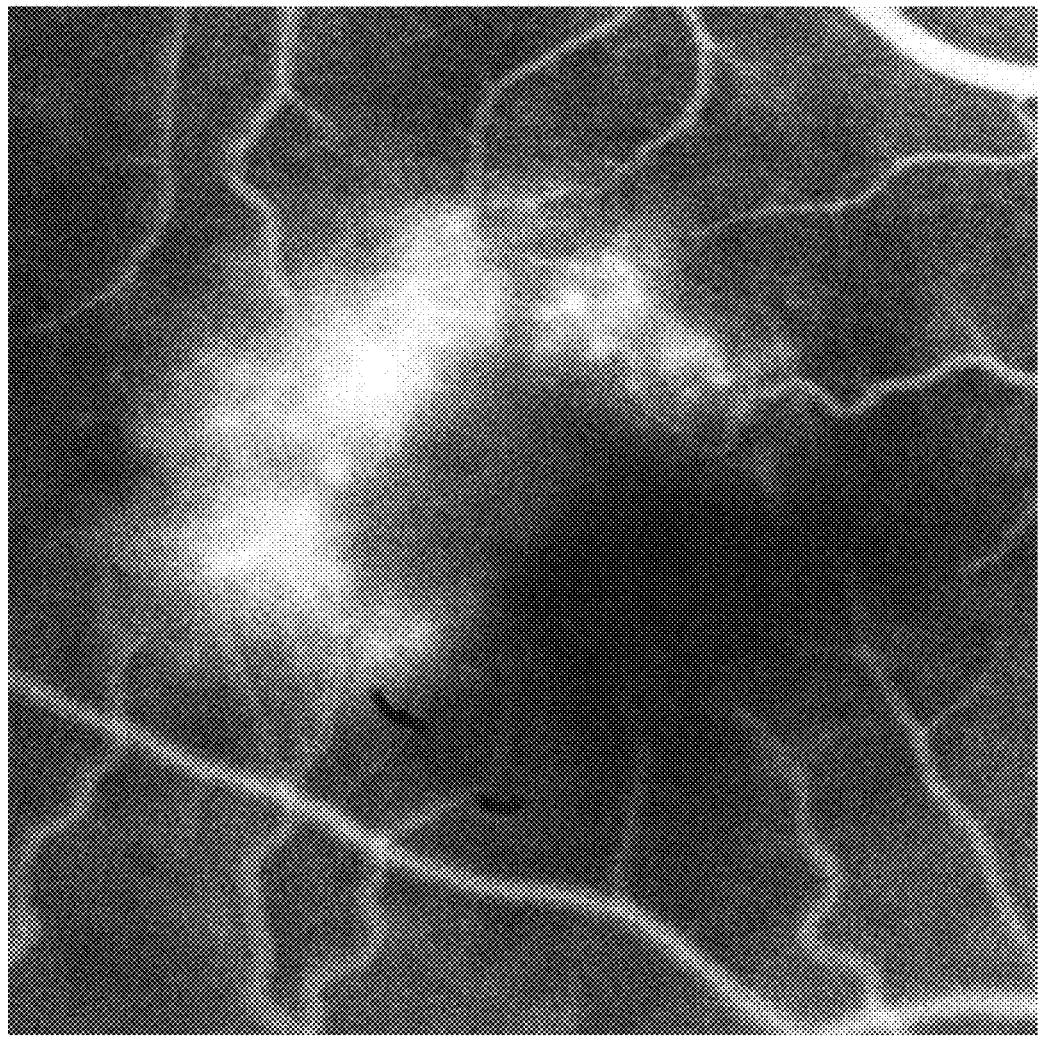
FIG. 13 is a fluorescein angiogram of an eye with macular telangiectasis.

FIG. 13 is a fluorescein angiogram of an eye with macular telangiectasis. The visualization of the vascular abnormalities is limited by the optical resolution of the fundus camera, the cataract present in the patient's eye, the dye leakage from the vessels, and the depth within the tissue the vascular abnormalities exist.

Figure 14:
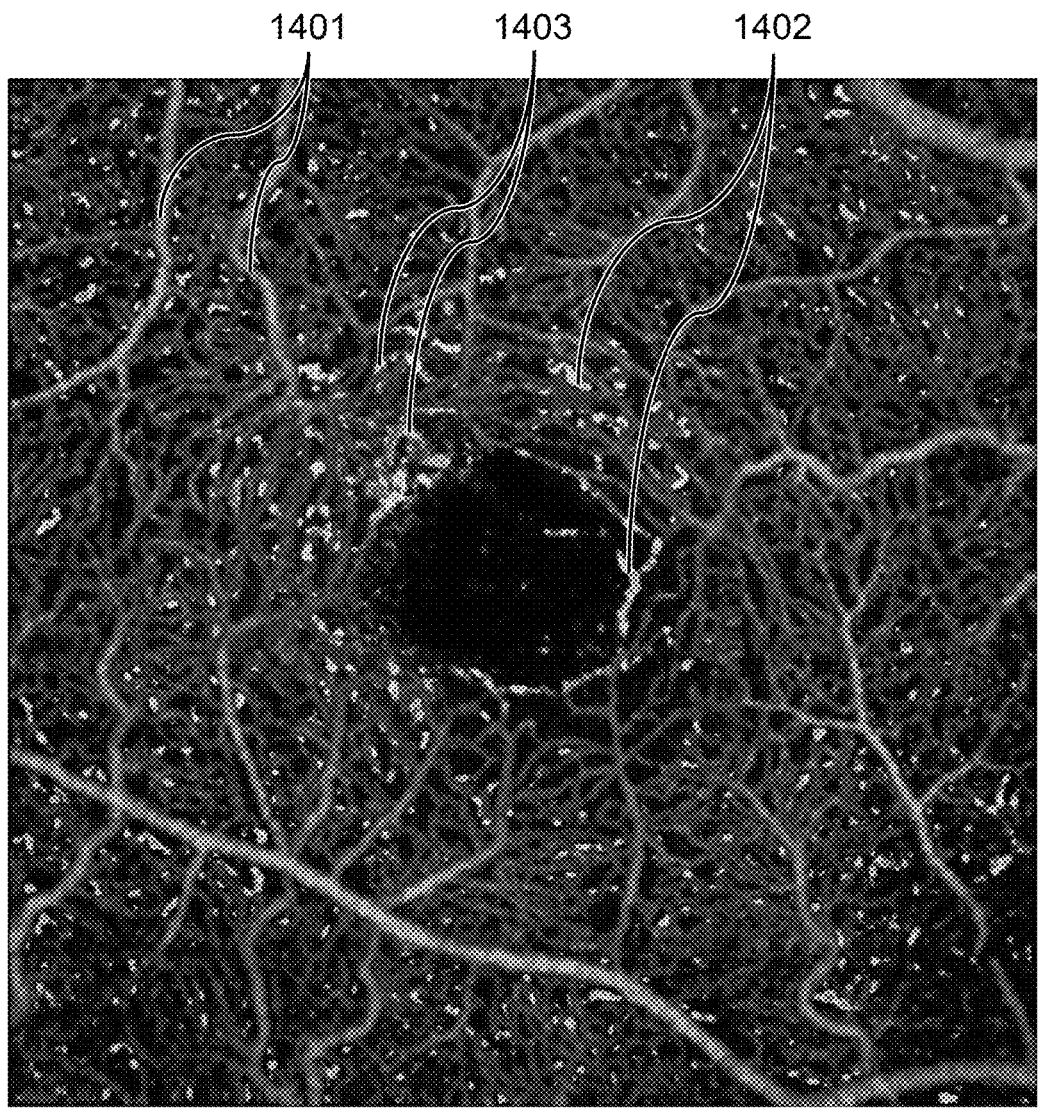
FIG. 14 is a top view of a color coded volumetric representation of the vascular abnormalities using techniques disclosed in this disclosure.

FIG. 14 is a top view of a color coded volumetric representation of the vascular abnormalities using techniques disclosed in this disclosure. The inner plexus of vessels (1401) is shown in blue, the deep plexus (1402) in red, and the vascular abnormalities deep to the deep plexus (1403) are shown in yellow. (FIG. 14 is rendered in grayscale; in the original color rendering, the abnormalities 1403 are sharply differentiated by their yellow color from the deep plexus 1402.)

Figure 15:
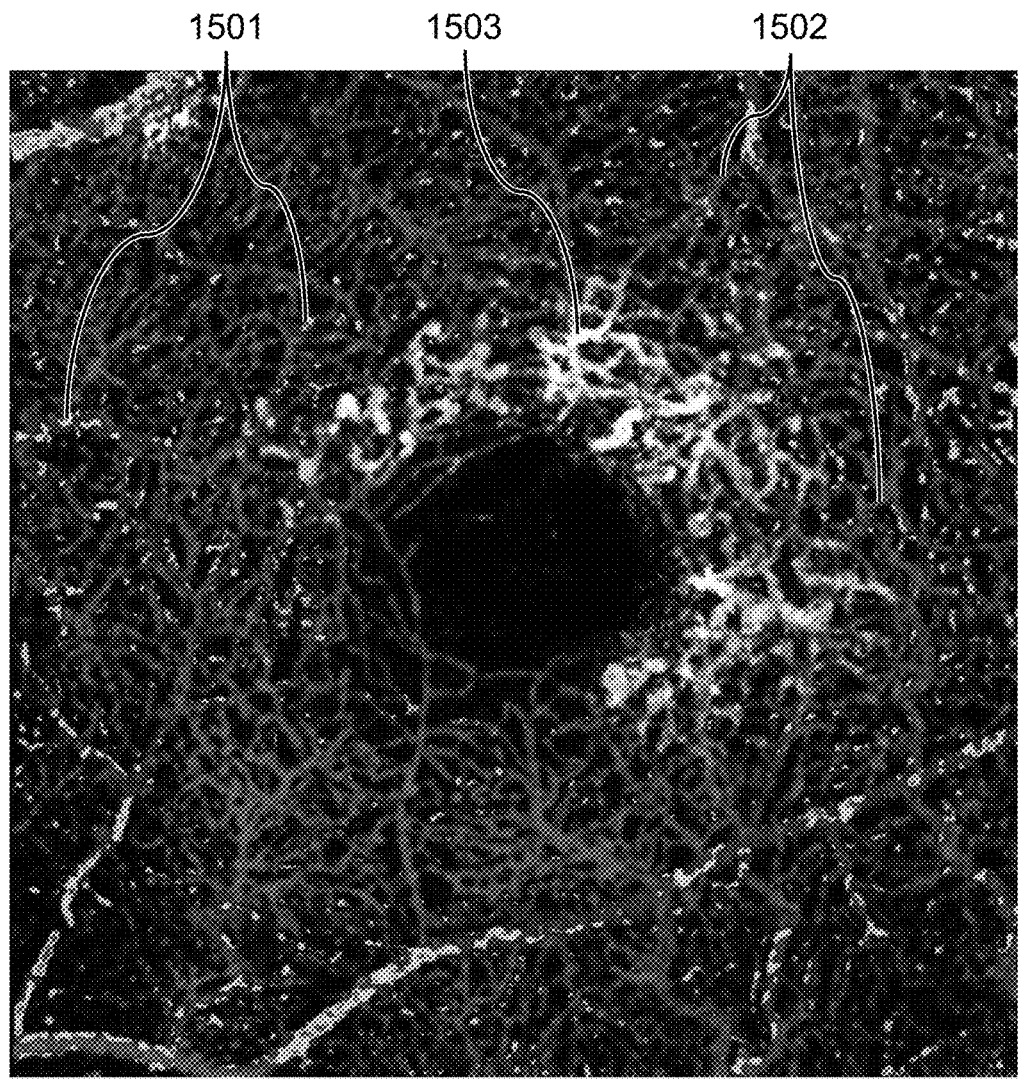
FIG. 15 is a bottom view of a color coded volumetric representation of the vascular abnormalities using techniques disclosed in this application.

FIG. 15 is a bottom view of a color coded volumetric representation of the vascular abnormalities using techniques disclosed in this application. The inner plexus of vessels (1501) is shown in blue, the deep plexus in red (1502), and the vascular abnormalities deep to the deep plexus are shown in yellow (1503). (In the grayscale rendering shown in FIG. 15, the red areas 1502 are depicted as darkest, the blue areas 1501 as lighter, and the yellow areas 1503, as the lightest areas, primarily to the right and above the center of the image.)

Figure 16:
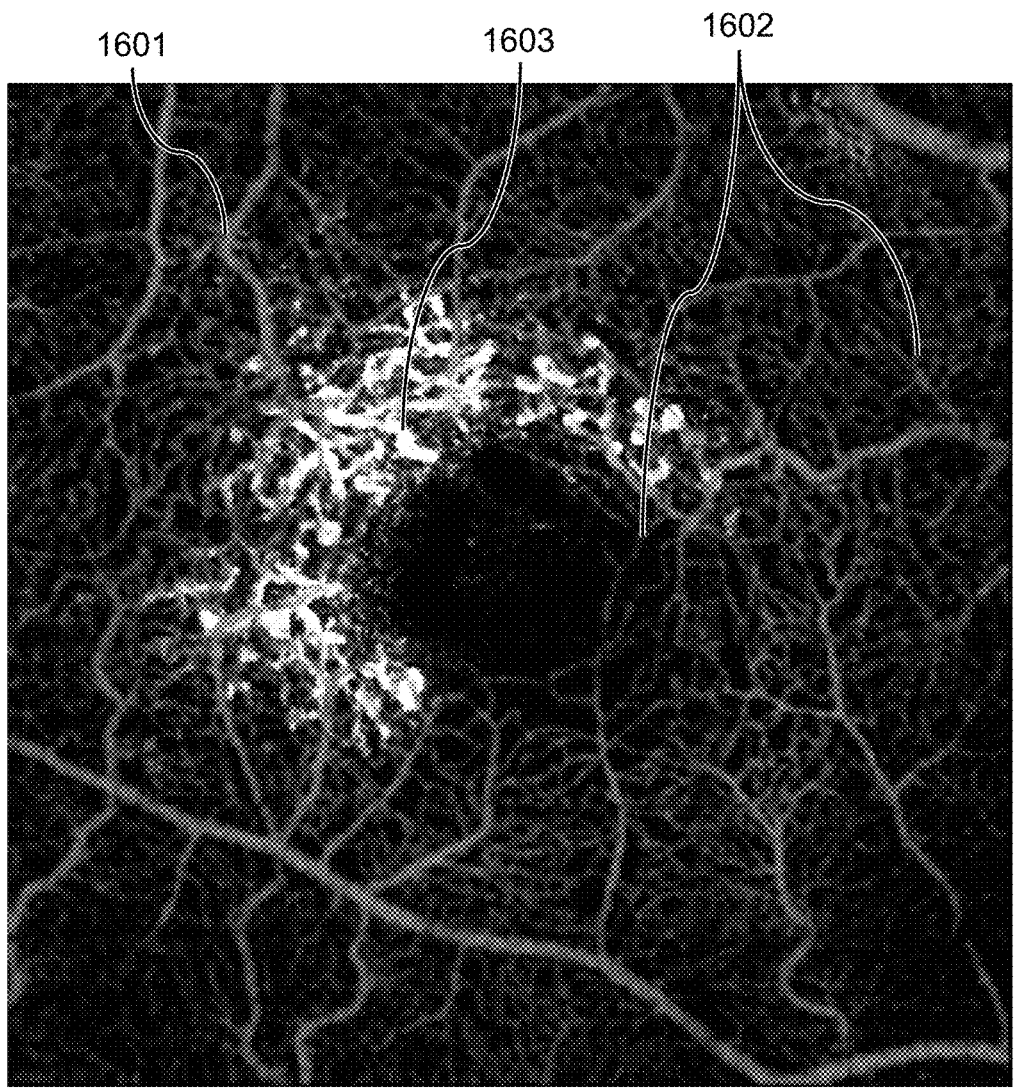
FIG. 16 is a top view of a color coded volumetric representation of the vascular abnormalities using techniques disclosed in this disclosure.

FIG. 16 is a top view of a color coded volumetric representation of the vascular abnormalities using techniques disclosed in this disclosure. The inner plexus of vessels (1601) is shown in blue, the deep plexus (1602) in red, and the vascular abnormalities deep to the deep plexus (1603) are shown in yellow. (In the grayscale rendering shown in FIG. 16, the darkest structures as rendered represent the red areas 1602, the blue elements 1601 are primarily larger vessels depicted as lighter than the red, and the yellow 1603 is the lightest of the areas, primarily above and to the left of the center of the image.) The opacity of the inner plexus and deep plexus were made partially transparent to show the abnormal vessels invading the deeper portions of the retina. Note the similar configuration to the hyperfluorescence seen in the fluorescein angiographic evaluation (FIG. 13). One main difference is the OCT angiographic image was made with no dye injection.

Figure 17A:
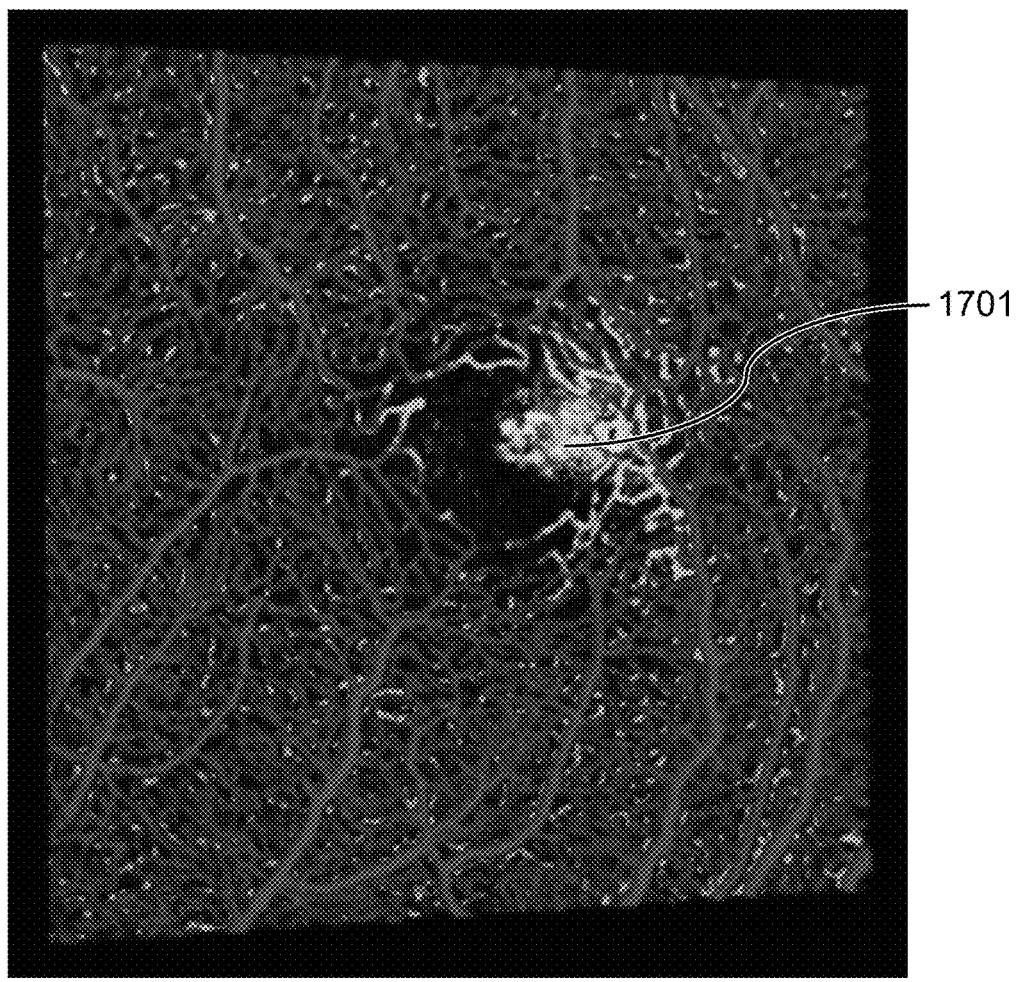
FIGS. 17A-17E show selected images from a movie showing a progression of rotated views of a colored rendering of layers, in an area with a cyst, the image of which was obtained by segmenting the structural OCT data. The region imaged here is 3×3×0.2 mm.
Figure 17B:
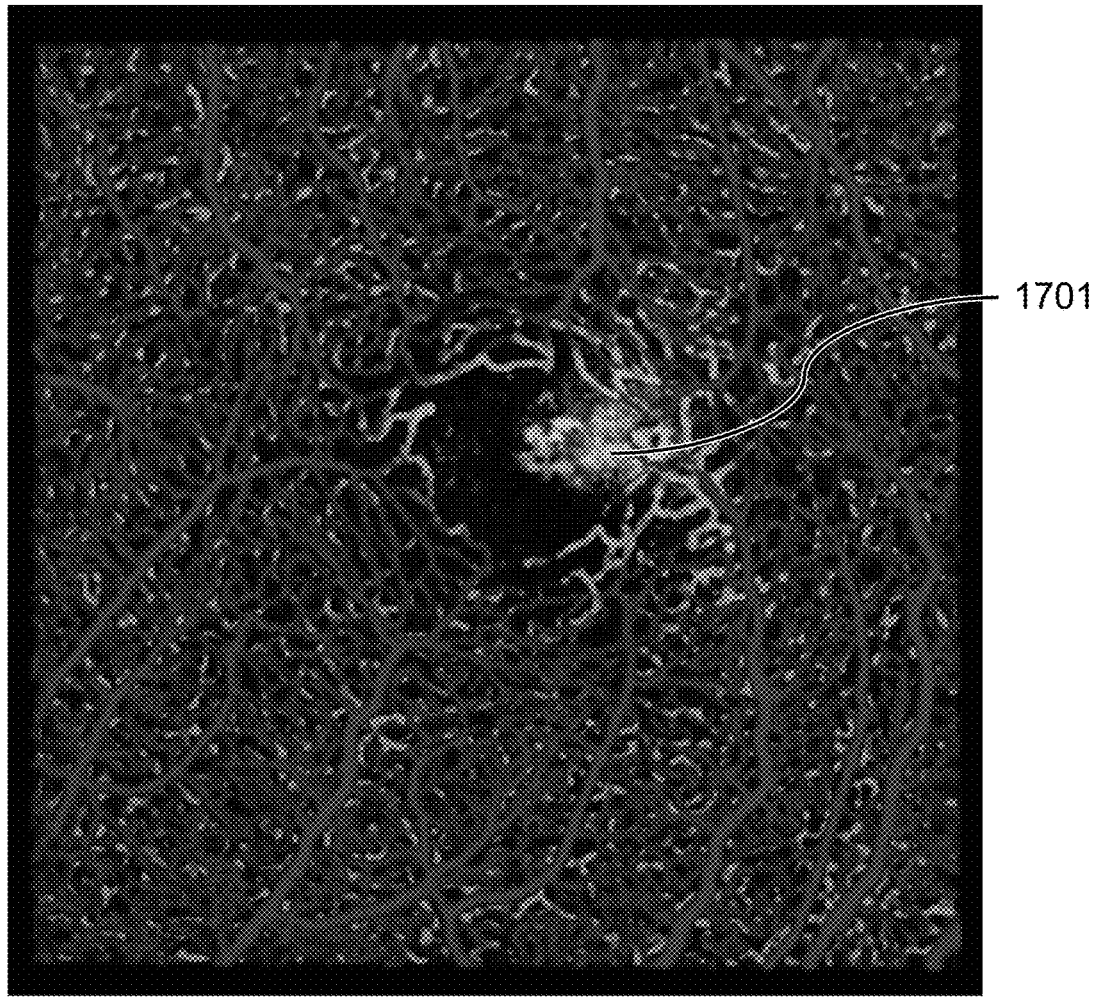
Figure 17C:
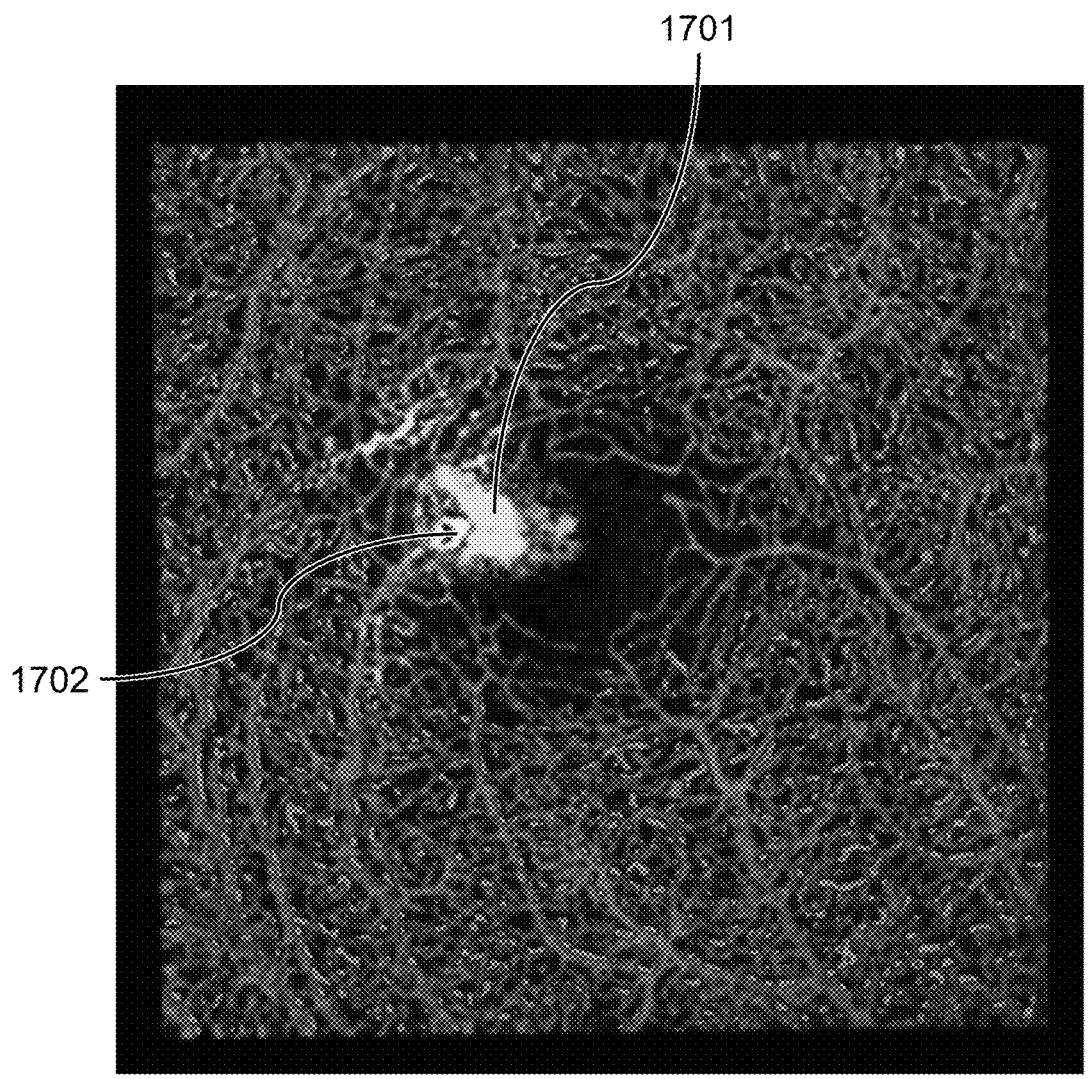
Figure 17D:
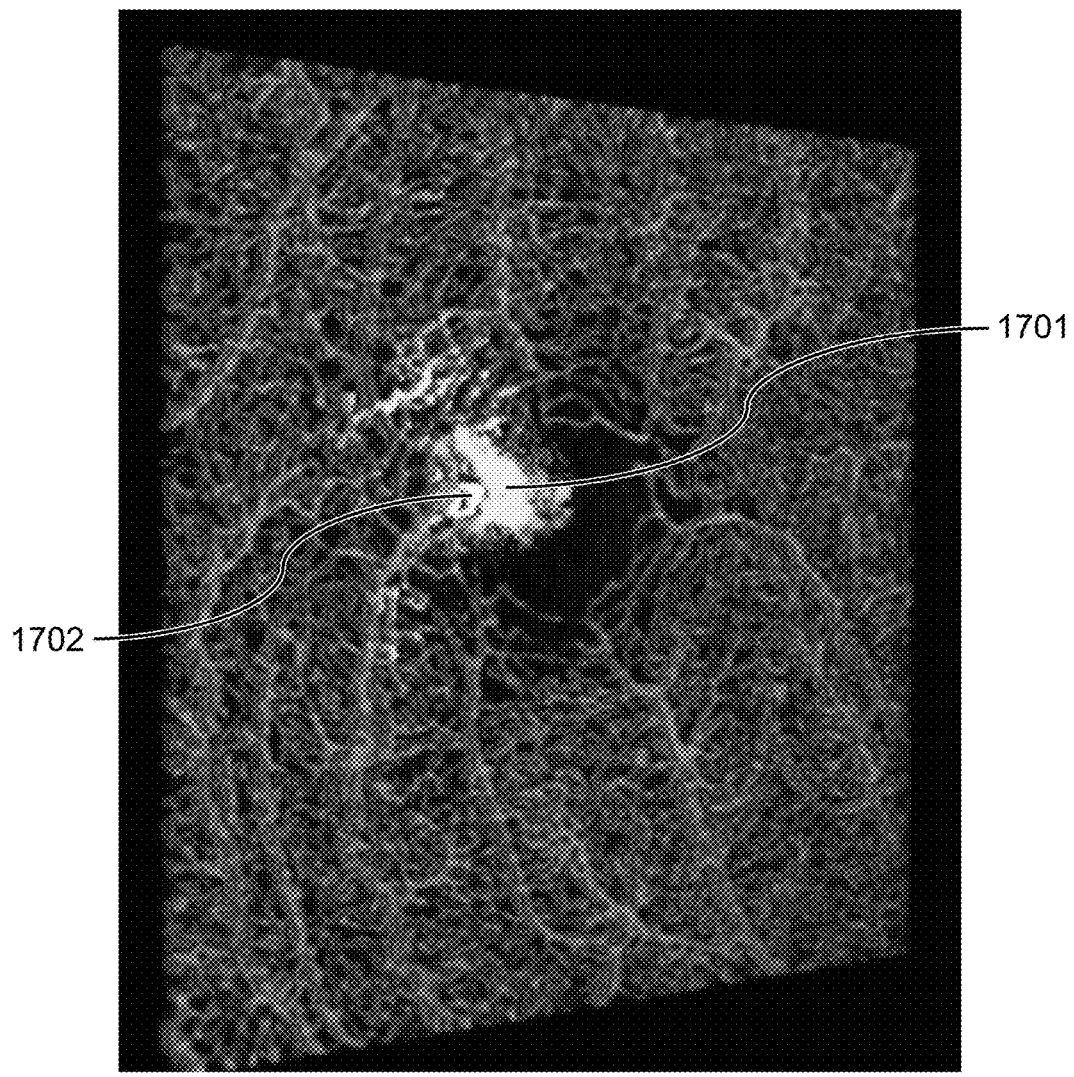
Figure 17E:
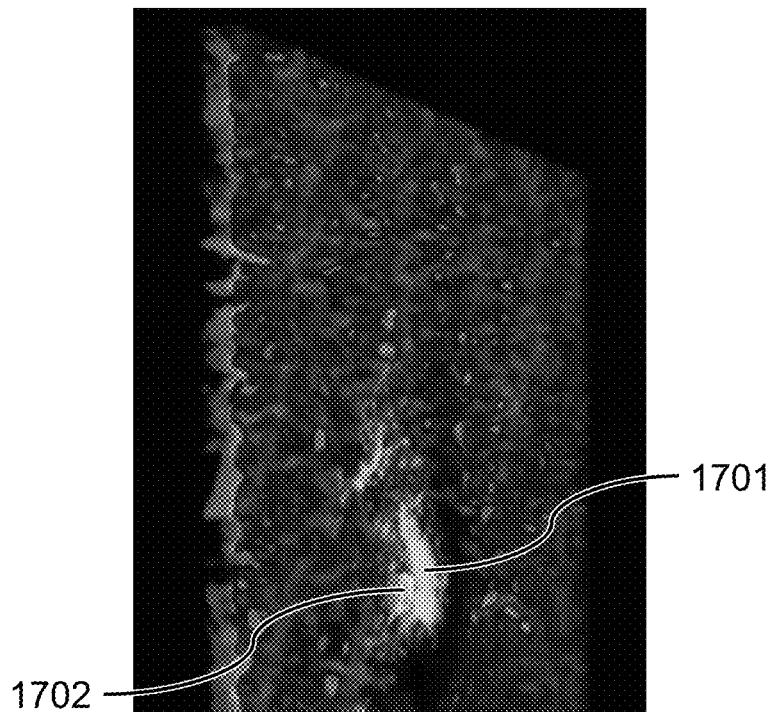

FIGS. 17A-17E are selected images from a movie showing a progression of rotated views of a colored rendering of layers, in an area with a cyst. The region imaged here is 3×3×0.2 mm. The disease shown is the same disease as shown in FIGS. 12-16. It is common to see a type of cystoid breakdown in the retina. That cystoid space (1701) is colored cyan in these images and the vessels are rendered as normal. The association between the cyst (1701) and the yellow vascular dilation (1702) is evident. (In the original image, the areas 1701 and the smaller area 1702, shown to the left of 1701 in FIGS. 17C, 17D, and 17E, is sharply differentiated by its yellow color from the cyan of area 1701.) Thus, pathology in the volume rendering can also be labelled with a color. This can be done independent of or in conjunction with OCT angiography.

The above description is intended to be illustrative, and not restrictive. Many other embodiments will be apparent to those of skill in the art upon reviewing the above description. The scope of the inventions described herein should, therefore, be determined with reference to the appended claims, along with the full scope of equivalents to which such claims are entitled.

A list of the references cited throughout this disclosure is also appended hereto as an appendix, incorporated in this disclosure by reference.

REFERENCES

1 Huang D, Swanson E A, Lin C P, Schuman J S, Stinson W G, Chang W, Hee M R, Flotte T, Gregory K, Puliafito C A, et al. Optical coherence tomography. Science. 1991; 254(5035):1178-81.

2 Hee M R, Izatt J A, Swanson E A, Huang D, Schuman J S, Lin C P, Puliafito C A, Fujimoto J G. Optical coherence tomography of the human retina. Arch Ophthalmol. 1995 Mar;113(3):325-32.

3 Fercher A F. Optical coherence tomography. J Biomed Opt. 1996;1(2):157-73.

4 Drexler W, Morgner U, Kärtner FX, Pitris C, Boppart S A, Li X D, Ippen E P, Fujimoto J G. In vivo ultrahigh-resolution optical coherence tomography. Opt Lett. 1999; 24(17):1221-3.

5 de Boer J F, Cense B, Park B H, Pierce M C, Tearney G J, Bouma B E. Improved signal-to-noise ratio in spectral-domain compared with time-domain optical coherence tomography. Opt Lett. 2003;28(21):2067-9.

6 Choma M, Sarunic M, Yang C, Izatt J. Sensitivity advantage of swept source and Fourier domain optical coherence tomography. Opt Express. 2003;11(18):2183-9

7 Leitgeb R, Drexler W, Unterhuber A, Hermann B, Bajraszewski T, Le T, Stingl A, Fercher A. Ultrahigh resolution Fourier domain optical coherence tomography. Opt Express. 2004;12(10):2156-65.

8 Drexler W, Fujimoto J G (eds.) Optical Coherence Tomography: Technology and Applications. Berlin, Springer, 2008, pp 1-1346.

9 Fingler J, Readhead C, Schwartz D M, Fraser S E. Phase-contrast OCT imaging of transverse flows in the mouse retina and choroid. Invest Ophthalmol Vis Sci. 2008;49(11):5055-9.

10 Mariampillai A, Standish B A, Moriyama E H, Khurana M, Munce N R, Leung M K, Jiang J, Cable A, Wilson B C, Vitkin I A, Yang V X. Speckle variance detection of microvasculature using swept-source optical coherence tomography. Opt Lett. 2008;33(13):1530-2

11 Mariampillai A, Leung M K, Jarvi M, Standish B A, Lee K, Wilson B C, Vitkin A, Yang VX. Optimized speckle variance OCT imaging of microvasculature. Opt Lett. 2010;35(8):1257-9.

12 Kim D Y, Fingler J, Werner J S, Schwartz D M, Fraser S E, Zawadzki R J. In vivo volumetric imaging of human retinal circulation with phase-variance optical coherence tomography. Biomed Opt Express. 2011;2(6):1504-13.

13 An L, Shen T T, Wang R K. Using ultrahigh sensitive optical microangiography to achieve comprehensive depth resolved microvasculature mapping for human retina. J Biomed Opt. 2011;16(10):106013.

14 Conroy L, DaCosta R S, Vitkin I A. Quantifying tissue microvasculature with speckle variance optical coherence tomography. Opt Lett. 2012;37(15):3180-2.

15 Jia Y, Tan O, Tokayer J, Potsaid B, Wang Y, Liu J J, Kraus M F, Subhash H, Fujimoto J G, Hornegger J, Huang D. Split-spectrum amplitude-decorrelation angiography with optical coherence tomography. Opt Express. 2012;20(4): 4710-25.

16 Mahmud M S, Cadotte D W, Vuong B, Sun C, Luk T W, Mariampillai A, Yang V X. Review of speckle and phase variance optical coherence tomography to visualize microvascular networks. J Biomed Opt. 2013;18(5): 50901.

17 Jia Y, Bailey S T, Wilson D J, Tan O, Klein M L, Flaxel C J, Potsaid B, Liu J J, Lu C D, Kraus M F, Fujimoto J G, Huang D. Quantitative optical coherence tomography angiography of choroidal neovascularization in age-related macular degeneration. Ophthalmology. 2014;121 (7):1435-44.

18 Frangi, A, Niessen, W, Vincken, K, Viergever, M: Multiscale vessel enhancement filtering. In Wells, W, Colchester, A, Delp, S, (eds.): MICCAI. Volume 1496 of Lecture Notes in Computer Science., Springer Berlin/Heidelberg, 1998; 130-137

19 Krissian, K, Malandain, G, Ayache, N, Vaillant, R, Trousset, Y: Model based detection of tubular structures in 3d images. Computer Vision and Image Understanding 80(2) 2000; 130-171

Russ J C. The Imaging Processing Handbook, Sixth Edition. CRC Press pages 1-885.

I claim:

1. A method of computer aided visualization and diagnosis comprising:
   acquiring an OCT dataset using a processor in conjunction with an imaging system;
   evaluating the dataset, with the processor, for flow information using amplitude or phase information;
   generating a matrix of voxel values, with the processor, representing flow occurring in vessels in the volume of tissue;
   performing volume rendering of these values, the volume rendering comprising deriving three dimensional position and vector information of the vessels with the processor;
   displaying the volume rendering information on a computer monitor, including generating depictions of the vessels; and
   using morphologic and reflectivity data in the assessment, including connectivity of voxels and feature characteristics, to classify the vessels.

2. The method of claim 1, further comprising assessing the vascularity, vascular density, and vascular flow parameters as derived from the volume rendered images.

3. The method of claim 1, further comprising providing user interface controls to rotate, shrink, and expand the volume rendered image of the vascular information from various angles and viewpoints.

4. The method of claim 1, further comprising registering 3D images obtained over time to obtain vascular flow information related to change over time.

5. The method in claim 4, wherein the pulsatility of flow is calculated on either a voxel or feature basis.

6. The method of claim 1, wherein said method is applied to the retina, choroid, optic nerve, and other vascular structures in the eye.

7. The method of claim 1, further comprising generating depictions of the vessels of the eye, and using fractal dimension to classify the vessels.

8. The method in claim 7, further comprising analyzing the classified vessels to provide a segmentation of vascular layers.

9. The method of claim 1 wherein the information displayed on the computer monitor is a 3D image, and further comprising integrating blood flow information through the 3D image to obtain qualitative and quantitative estimates of blood flow, and representing said estimates as a qualitative or quantitative overlay on the 3D image.

10. The method of claim 8, further comprising using vessel flow information and vascular density determined from said method to derive tissue perfusion information in a volume of selected tissue.

11. The method of claim 10, further comprising color coding the vessels to show perfusion or flow information.

12. The method of claim 9 wherein the data is visually represented on the computer monitor in orthogonal planes to show regional perfusion status.

13. The method of claim 9 wherein the qualitative and quantitative estimates of blood flow are obtained by integration of flow information through the cross-section of the flow data visualized.

14. The method of claim 10, further comprising classifying perfusion in the retinal nerve fiber layer as a means to diagnose or monitor glaucoma.

15. The method of claim 10, further comprising classifying and grading the perfusion in the retina to diagnose or monitor diabetic retinopathy, artery occlusions, vein occlusions, or other retinal vascular disease.

16. The method in claim 10, further comprising deriving a numerical perfusion index for use to monitor health and disease of the retina.

17. The method of claim 16, further comprising displaying, numerically or graphically, deviations from normal values.

18. The method of claim 1 wherein structural information from the OCT dataset is segmented and displayed with the flow data in the volume rendering, thereby placing the structural data in proper anatomic orientation and position in relation to the vessels.

19. The method of claim 18 wherein the resultant vascular flow parameters are shown embedded in structural OCT data showing the retinal anatomy.

20. The method of claim 18, further comprising color coding the segmented anatomic structures, or otherwise visually depicting them in a highlighted manner, to increase recognition and facilitate visualization.

21. The method of claim 20, further comprising calculating the volume of the segmented anatomic structures.

22. The method of claim 18, further comprising using reflective or morphologic characteristics such as gray scale values, diameter, circularity, or analysis such as use of Frangi filters, to generate automatic classifications of the structural features segmented.

23. The method of claim 20, wherein regions of either normal or abnormal vascularity in terms of vessel density may be specifically highlighted in relation to structural OCT findings.

24. The method of claim 23, further comprising segmenting a tumor in the structural OCT dataset and displaying the vessels in that tumor with a different or distinctive color scheme.

25. The method of claim 20 wherein the transparency of the volume rendered image is modified according to local vascular density and perfusion data.

26. The method of claim 25, wherein the modification of transparency of the volume rendered image comprises variation by layer or depth.

27. The method of claim 26, further comprising increasing the transparency of overlaying layers to increase visibility of deeper layers.

28. The method of claim 20 wherein the color of the volume rendered image is modified according to local vascular density and perfusion data.

29. The method of claim 20 wherein the tissue, the flow information or any combination is displayed in a manner to visualize depth information through the tissue sampled.

30. The method of claim 29, further comprising the use of 3D monitors or anaglyph representations.

31. The method of claim 20 further comprising color coding areas of pathology.

32. The method of claim 1, further comprising further evaluating the vessels by examining their tubularity and connectivity to adjacent voxels.

33. The method of claim 1 further comprising removing noise by 2D and 3D methods.

34. A system for computer aided visualization and diagnosis comprising:

an imaging system under the control of at least one processor for acquiring an OCT dataset from a volume of anatomical tissue; and software stored on a computer-readable medium accessible to the at least one processor, containing instructions to cause the at least one processor to:

evaluate the dataset for flow information using amplitude or phase information;
- generate a matrix of voxel values, representing flow occurring in vessels in the volume of tissue;
- perform volume rendering of these values by deriving three dimensional position and vector information of the vessels; and
- display the volume rendering information on a computer monitor, including generating depictions of the vessels; and
- use morphologic and reflectivity data in the assessment, including connectivity of voxels and feature characteristics, to classify the vessels.

35. A non-transitory computer readable medium containing recorded instructions to cause a processor to:
- acquire from an imaging system an OCT dataset from a volume of anatomical tissue;
- evaluate the dataset for flow information using amplitude or phase information;
- generate a matrix of voxel values, representing flow occurring in vessels in the volume of tissue;
- perform volume rendering of these values by deriving three dimensional position and vector information of the vessels; and
- display the volume rendering information on a computer monitor, including generating depictions of the vessels; and
- use morphologic and reflectivity data in the assessment, including connectivity of voxels and feature characteristics, to classify the vessels.

* * * * *